(12) United States Patent
Furukawa

(10) Patent No.: US 7,301,630 B2
(45) Date of Patent: Nov. 27, 2007

(54) LIGHT SCATTERING ANALYSIS AND MEASUREMENT

(75) Inventor: Hidemitsu Furukawa, Ebetsu (JP)

(73) Assignee: Gel-Design Inc., HoKKaido (JP)

( * ) Notice: Subject to any disclaimer, the term of this patent is extended or adjusted under 35 U.S.C. 154(b) by 249 days.

(21) Appl. No.: 11/070,270

(22) Filed: Mar. 3, 2005

(65) Prior Publication Data

US 2006/0044558 A1 Mar. 2, 2006

(30) Foreign Application Priority Data

Sep. 2, 2004 (JP) ............................. 2004-256056

(51) Int. Cl.
G01N 21/00 (2006.01)
(52) U.S. Cl. ...................................... 356/338; 356/342
(58) Field of Classification Search ................ 356/338, 356/342, 343
See application file for complete search history.

(56) References Cited

U.S. PATENT DOCUMENTS 5,752,519 A * 5/1998 Benaron et al. ............ 600/476

OTHER PUBLICATIONS

Furukawa, H., et al., "Swelling-induced Modulation of Static and Dynamic Fluctuations in Polyacrylamide Gels observed by Scanning Microscopic Light Scattering", *Physical Review E*, pp. 031406-1-031406-14, (2003).

Furukawa, H., et al., "Characterization of Fine Network Structure in Polymar Gels with Scanning Microscope Light Scattering", *Japanese Journal of Polymer Science and Technology*, vol. 59, No. 10, pp. 578-589, (Oct. 2002).

Furukawa, H., et al., "Dynamic Light Scattering from Static and Dynamic Fluctuations in Inhomogeneous Media", *Journal of the Physical Science of Japan*, vol. 71, No. 12, pp. 2873-2880, (2002).

Aberle, L.B., et al., "Effective suppression of multiply scattered light in static and dynamic light scattering", *Applied Optics*, vol. 37, No. 27, pp. 6511-6524, (Sep. 1998).

Otsuka Electronics Co. Ltd., "Fiber-optics particle analyzer FPAR-1000", www.photal.co.jp/product/fpar_0.html, and English version searched on www.photal.co.jp/english/product/fpar.html, (Aug. 24, 2006).

Weitz, D.A., et al., "Diffusing-wave spectroscopy", *W Brown ed.*, Oxford Science Pub., Ch. 16, pp. 652-720, (1993).

* cited by examiner

*Primary Examiner*—Roy M. Punnoose
(74) *Attorney, Agent, or Firm*—The Nath Law Group; Jerald L. Meyer; Stanley N. Protigal

(57) ABSTRACT

A light scattering apparatus capable of measuring light scattering of opaque samples. In the apparatus, control section 190 controls an optical path length required for laser light output from laser light source 210 to being incident on a sample and then outgoing as scattered light to approximate by zero. Detector 330 detects outgoing scattered light to output as a photon pulse. Pulse interval measurer 350 measures a time interval of the photon pulse output from detector 330. An operator in computer 360 calculates an n-order correlation function (n1) using the time interval of the photon pulse measured in pulse interval measurer 350.

18 Claims, 17 Drawing Sheets

LIGHT SCATTERING ANALYSIS AND MEASUREMENT

BACKGROUND OF THE INVENTION

1. Field of the Invention

The present invention relates to a light scattering apparatus and light scattering measurement method, and more particularly, to a light scattering apparatus and light scattering measurement method enabling measurement even when a sample to measure is opaque.

2. Description of Related Art

A dynamic light scattering method is to analyze a fine structure and motion characteristics inside a solution by measuring thermal motion occurring inside the solution through the light scattering phenomenon. Generally, measurement using light is difficult to measure a structure under wavelengths of the light in principle. However, the dynamic light scattering method is to measure an internal structure through thermal motion, and therefore, enables measurement of a fine structure under wavelengths of the light (from 0.1 nm up to and including 1 μm). Accordingly, the dynamic light scattering method using visible laser light source relatively safe to human bodies is a convenient observing method enabling determination of a size of a particle dispersed inside a solution and of a network structure of gel. The dynamic light scattering method has widely been used as a method to directly measure a particle size in a solution-state in a transparent particle dispersion system.

For example, as a practical application, it has been tried earlier applying the dynamic light scattering method to measurement of transparent samples with complicated structures such as liquid crystal, gel and colloid, but, no practical use has been known currently. This is because scattered light from liquid crystal or gel inevitably includes an excessive component caused by inhomogeneity of an internal structure, and there is a problem that no method exists to evaluate such a component accurately.

In recent years, in order to solve such a problem, a method has newly been developed to determine a measurement amount of static average (ensemble average) with time average and spatial average properly carried out in close consideration of an excessive component of scattered light caused by inhomogeneity using a scanning microscopic scattering method. See Document 1 (H. Furukawa, K. Horie, R. Nozaki and M. Okada "Swelling-induced modulation of static and dynamic fluctuations in polyacrylamide gels observed by scanning microscopic light scattering", Phys. Rev. E, 68, 2003, p. 031406-1 to 031406-14), Document 2 (H. Furukawa and K. Horie "Characterization of a fine network structure of a polymer gel by scanning microscopic light scattering", Japanese Journal of Polymer Science and Technology, Vol. 59, 2002, p. 578-589). Thus, the method has been established for measuring a transparent sample with a complicated fine structure using a visible light source. Further, Document 3 (H. Furukawa and S. Hirotsu, "Dynamic Light Scattering from Static and Dynamic Fluctuations in Inhomogeneous Media", J. Phys. Soc. J., 71, 2001, p. 2873-2880) describes precisely deriving a mathematical formula necessary to determine specifically an ensemble average correlation function. In this way, practical methods have been established for directly measuring a fine internal structure of a transparent sample with a complicated internal structure using a visible light source.

However, the aforementioned methods are not effective as a method for measuring an internal state of an opaque gel substance or colloidal solution including food such as milk and pudding and cosmetics such as shampoo and conditioner. In the dynamic light scattering method, measurement of a fine internal structure is easy in transparent samples using visible light, but difficult in opaque samples (including samples with high turbidity). A phenomenon of being cloudy is a phenomenon where a substance seems to be opaque because strong scattering occurs and causes multiple scattering such that scattered light is scattered again. Accordingly, specific consideration is required to detect light that is scattered only once as in the general light scattering method.

Conventionally, as a method of overcoming such a problem, there have been a method of removing the contribution of multiple scattering using two laser beams, and a method of measuring in close proximity to a surface to ignore multiple scattering. See, respectively, Document 4 (L. B. Aberie, P. Hulstede, S. Wiegand, W. Schroer and W. Staude, "Effective suppression of multiply scattered light in static and dynamic scattering", Applied Optics, 37, 1998, p. 6511-6524), and Document 5 (Otsuka Electronics Co., Ltd. "Fiber-Optics Particle Analyzer FPAR-1000", online, Searched Aug. 1, 2004, [http://www.photal.co.jp/product/fpar_0.html]). However, it is known that the former is complicated and expensive and therefore not spread widely, and that the latter is commercially available, but cannot obtain accurate measurements because the means for overcoming the problem is too simplified.

Meanwhile, there is theoretical consideration already about what scattering occurring inside an opaque sample, suggesting that analyzing multiply scattered light enables in principle examination of thermal motion inside a sample.

However, it is necessary to know the number of scattering times N of multiple scattering occurring inside a sample in applying the theory to examine thermal motion inside the sample by analyzing multiply scattered light. Determining the number of scattering times N is difficult both theatrically and experimentally, and therefore, examining internal thermal motion is difficult in principle in a state where multiple scattering occurs. Further, the number of scattering times N is an average amount, and the accurate number of times cannot be determined. Accordingly, even if a method is established of assuming the number of scattering times N experimentally, problems arise such that an internal structure is only determined within some error range in existing theories even using such a method.

Further, in order to perform inexpensive practical analysis, it is required to promptly process time-series data of an enormous amount of photon pulses measured in dynamic light scattering. A specific analysis apparatus has widely been used in processing of time-series data for accurate measurement, is high in evaluation, but expensive. The analysis apparatus is a light scattering dedicated calculator in which all calculation portions are made of logic circuits (so-called full-logic), which are complicated circuits, resulting in limitations in reduction in manufacturing cost.

SUMMARY OF THE INVENTION

It is an object of the present invention to provide a light scattering apparatus and light scattering measurement method enabling measurement of opaque samples.

It is another object of the invention to provide an inexpensive practical light scattering analysis apparatus and light scattering measurement analysis method for calculating a photon correlation function from time-series data of photon pulses measured in light scattering.

According to an aspect of the invention, a light scattering apparatus is provided with a laser light source that emits laser light, control means for controlling an optical path length required for the laser light incident on a sample to being outgoing as scattered light to approximate by zero, and detection means for detecting outgoing scattered light to output a photon pulse.

According to another aspect of the invention, a light scattering measurement analysis apparatus is provided with input means for inputting a time interval of photon pulses obtained by measuring scattered light that is laser light incident on a sample and then scattered on each of a plurality of optical path lengths, and operation means for calculating a photon correlation function corresponding to each of the plurality of optical path lengths using the time interval of photon pulses, extrapolating an n-order correlation function ($n \geq 1$) obtained from the calculated photon correlation function, and thereby calculating an n-order correlation function with an optical path length of zero.

According to still another aspect of the invention, a light scattering measurement method is provided with a controlling step of controlling an optical path length required for laser light incident on a sample to being outgoing as scattered light to approximate by zero, and a detection step of detecting outgoing scattered light.

According to still another aspect of the invention, a light scattering measurement method is provided with a controlling step of controlling an optical path length required for laser light incident on a sample to being outgoing as scattered light to a plurality of optical path lengths ranging from zero to a predetermined range, and a detection step of detecting outgoing scattered light on each of the plurality of optical path lengths.

According to still another aspect of the invention, a light scattering measurement analysis method is provided with an input step of inputting a time interval of photon pulses obtained by measuring scattered light that is laser light incident on a sample and then scattered on each of a plurality of optical path lengths, and an operation step of calculating a photon correlation function corresponding to each of the plurality of optical path lengths, extrapolating an n-order correlation function ($n \geq 1$) obtained from the calculated photon correlation function, and thereby calculating an n-order correlation function with an optical path length of zero.

BRIEF DESCRIPTION OF THE DRAWINGS

The above and other objects and features of the invention will appear more fully hereinafter from a consideration of the following description taken in connection with the accompanying drawings, in which.

DESCRIPTION OF THE PREFERRED EMBODIMENT

Embodiments of the present invention will specifically be described below with reference to accompanying drawings.

Figure 1:
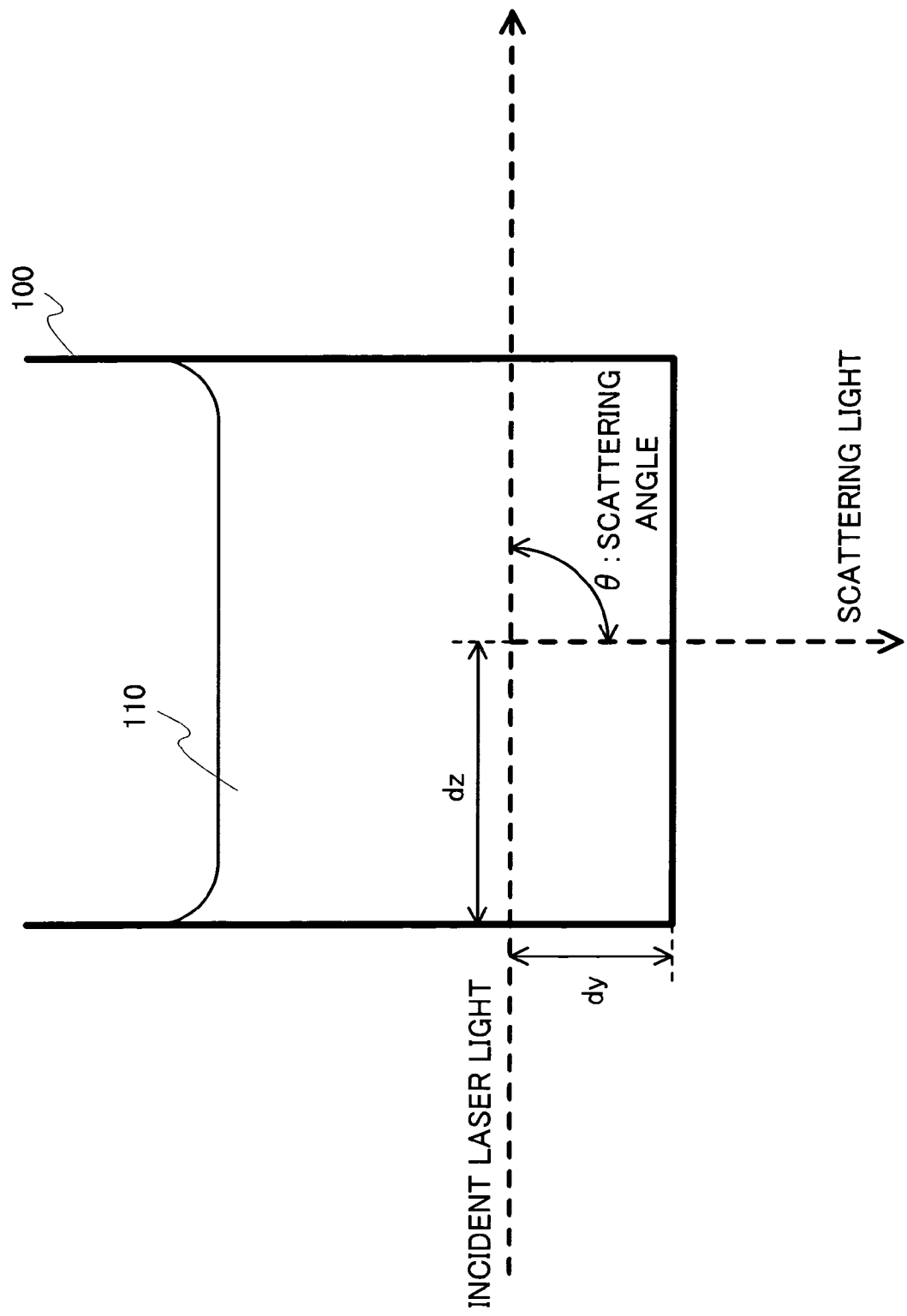
FIG. 1 is a view showing the relationship between a sample cell and laser light in a light scattering apparatus and light scattering measurement method according to the present invention.
Figure 2:
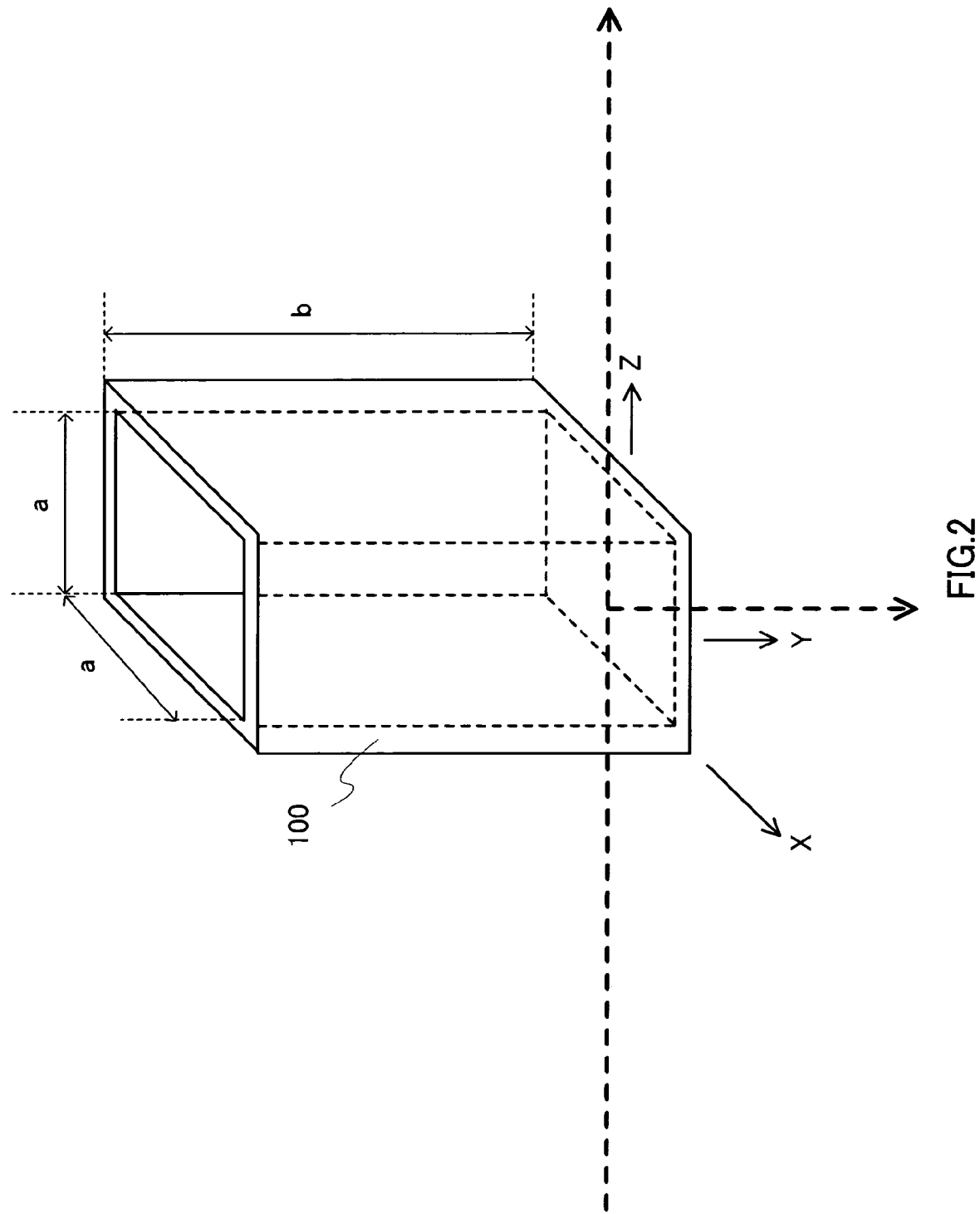
FIG. 2 is a view showing the cell in three dimensions.

FIG. 1 is a view showing the relationship between sample cell and laser light in a light scattering apparatus and light scattering measurement method according to the present invention. FIG. 2 is a view showing an example of sample cell 100 in three-dimensions. In following descriptions, positions of structural elements and the like may be indicated using the XYZ axes. Directions of the XYZ axes are as shown in FIG. 2.

Sample cell 100 is a transparent container into which a sample to measure is inserted. As an example, a quartz cell with five transparent faces is used as sample cell 100. For example, as shown in FIG. 2, sample cell 100 has an inner size of a×a×b. In following descriptions, positions of sample cell 100 may be indicated using the XYZ axes. Directions of the XYZ axes are as shown in FIG. 2.

Sample 110 is a substance targeted for measurement, and may be a transparent or opaque sample, and examples of sample 110 include solid, liquid crystal, gel, colloid, polymer solution, polymer melting liquid, electrolytic solution and solution in which fine particles are dissolved such as microorganism, organelles and intracellular traits. Further, "being opaque" and "having turbidity" are the same with respect to multiple scattering of laser light, and not distinguished.

Incident laser light indicates the laser light incident on sample cell 100, and scattered light indicates the laser light scattered when the incident laser light is passed through sample 110 in sample cell 100.

The incident laser light is incident from the left as viewed in FIG. 1. It is assumed that the direction in which the incident laser light is incident is the Z-axis direction, and that the direction perpendicular to the incident laser light is the Y-axis direction. Herein, dz is an incident depth of the incident laser light in the Z-axis direction, and dy is an incident depth of the incident laser light (scattered light) in the Y-axis direction. "dz" may have a size in a range of zero to a. "dy" may have a size in a range of zero to b, but currently, a value around 1 mm is the minimum. The optical path length l is the sum of depths of two incident light beams, where $l=(dz+dy/\sin \theta)$. The scattered light forms an angle of scattering angle θ with respect to the incident laser light, and scatters in the Y-axis direction. "θ" takes values ranging from 0 to 180°, and this specification uses the case where θ is 90° due to the reason described below. When θ=90°, sin θ=1, and the optical path length l is the sum of dz and dy (l=dz+dy).

In the measurement theory of the light scattering apparatus and light scattering measurement method according to the invention, light scattering is measured while varying the optical path length l even under conditions where multiple scattering may occur, a position of a sample cell is controlled (scanned) so that the optical path length l is approximated by zero, thereby reducing the number of scattering times N of multiple scattering, and measurement of single scattering is thus allowed under the extreme condition where the optical path length l is zero. The measurement theory will be described later after descriptions of the light scattering apparatus.

Figure 3:
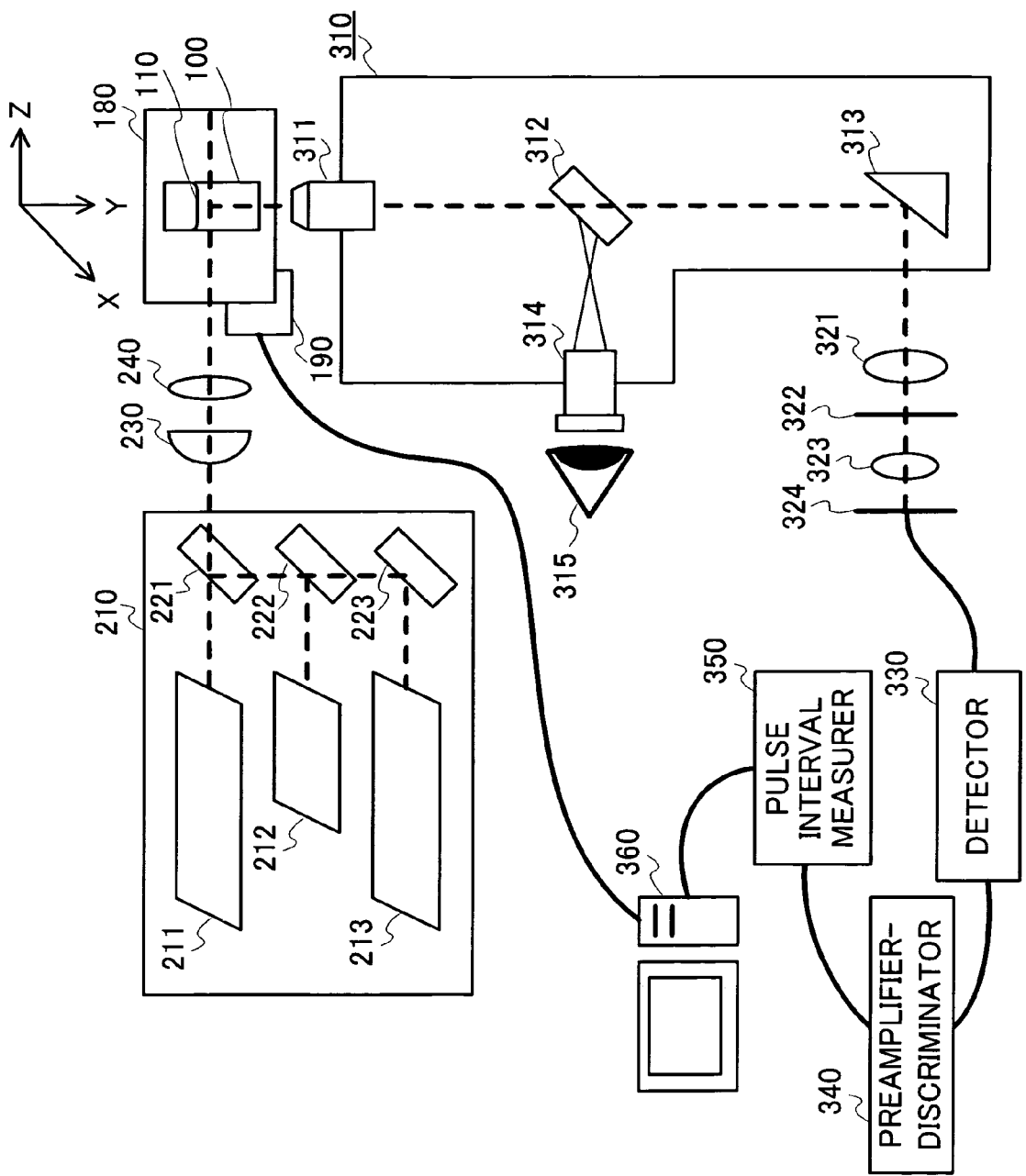
FIG. 3 is a view showing an example of a configuration of the light scattering apparatus.

An example of the light scattering apparatus will be described below. FIG. 3 is a view showing an example of a configuration of the light scattering apparatus. Structural elements assigned the same reference numerals as in FIG. 1 are the same as those in FIG. 1, and descriptions thereof are omitted.

Cell holder 180 stores sample cell 100.

Control section 190 moves a position of sample cell 100 in three dimensions. Using coordinates of the XYZ axes with coordinate axes shown in FIG. 3, control section 190 moves the position of sample cell 100 (actually, moves cell holder 180 to move sample cell 100).

Laser light source 210 emits laser light. In the example in FIG. 3, laser light source 210 emits three kinds of laser light. First light source 211, second light source 212 and third light source 213 emit laser light with respective different wavelengths. Half-mirrors 221 and 222 and total-reflection mirror 223 are arranged so that the three kinds of laser light are emitted in time division.

Cylindrical plano convex lens 230 gathers laser light. Polarizing plate 240 is a filter to remove extra components except vertically polarized light.

Inverted light microscope 310 is used to adjust an optical path. Inverted light microscope 310 is provided with objective lens 311, optical path switching section 312, rectangular prism 313 and visual observation section 314. Visual observation section 314 is to observe a state of sample 110 by user eye 315.

Objective lens 311 gathers scattered light scatted from sample cell 100.

Optical path switching section 312 switches optical paths and enables visual observation and measurement.

Rectangular prism 313 changes an optical path perpendicularly.

Visual observation section 314 enables visual observation of an optical path by optical path switching section 312 to perform visual observation of sample 110.

Polarizing plate 321 is a filter to remove extra components except vertically polarized light. Pinholes 322 and 324 are optical devices with small holes, and perform functions of selecting vertically scattered light from the incident laser light to pass. Concave lens 323 improves efficiency of scattered light. The pinholes are an example of passing means for passing the scattered light. As the passing means, a slit or the like may be used other than the pinhole.

Detector 330 converts photons included in the scattered light passed through pinhole 324 into photon pulses (optical pulse signal). In addition, pinhole 324 and detector 330 are connected with an optical fiber. Expected as the photon pulses herein are an electric signal with a pulse width of about 50 ns (short current pulse). A large number of pulses per unit time result in output of successive current.

Preamplifier-discriminator 340 amplifies a photon pulse, discriminates between the photon pulse and others, and passes only the photon pulse.

Pulse interval measurer 350 receives the photon pulse detected by detector 330 via preamplifier-discriminator 340, and measures a time interval of photon pulses.

Computer 360 controls a position of sample cell 100 using three-dimensional position information in the XYZ-axes directions, while calculating the photon correlation function from the time spacing of photon pulses. Actually, control of the position of sample cell 100 is carried out by operating control section 190 by instructions from computer 360, where control section 190 changes a position of cell holder 180. Calculation of the photon correlation function will be described later together with measurement of the time spacing of photon pulses.

The operation of the light scattering apparatus with the aforementioned configuration will be described below with reference to FIG. 3. Computer 360 determines a position of sample cell 100 to generate position information, and notifies control section 190 of the position information, and control section 190 adjusts a position of cell holder 180 based on the notified position information.

Laser light is emitted from either first light source 211, second light source 212 or third light source 213 of laser light source 210. The emitted laser light is gathered by cylindrical plano convex lens 230, passed through the filter function of polarizing plate 240, and incident on sample cell 100 as incident laser light. A user switches between three kinds of laser light. It is possible to switch laser light by computer.

Part of the incident laser light is incident on the objective lens as scattered light. The scattered light incident on the objective lens is passed through optical path switching section 312 comprised of a half mirror and rectangular prism 313, and extra components of the light except the vertically polarized light are removed by polarizing plate 321. Pinhole 322 selects scattered light that is scattered perpendicularly to the incident laser light. The scattered light is passed through the optical fiber via convex lens 323 and pinhole 324, and reaches detector 330. Photons included in the scattered light input to detector 330 are converted into photon pulses and output.

The photon pulses are input to pulse interval measurer 350 via preamplifier-discriminator 340, and the time spacing of photon pulses is measured. The measured time spacing is input to computer 360, and the photon correlation function is calculated. The processing in pulse interval measurer 350 and computer 360 will be described later. The general operation in the light scattering apparatus is as described above.

Measurement principles of the present invention will be described below with reference to FIGS. 1 to 3. A method is first discussed of overcoming multiple scattering using existing theories to measure light scattering. The number of scattering times N of multiple scattering is dependent on optical path length l, i.e. incident depths dz and dy of incident laser light. It is found out by considering the theory of multiple scattering that the scattering vector is in agreement with the wave number vector when the scattering angle is 90°, only in this case N becomes 1 under the extreme condition where the optical path length l is 0, and that the multiple scattering precisely agrees with general dynamic light scattering. Therefore, measurement is carried out in a plurality of positions from deep positions to shallow positions while varying the incident depth, the data is extrapolated to zero on optical path length l, and thus is determined the photon correlation function of scattered light intensity obtained in general dynamic light scattering. The summary is as described above.

The measurement principles will be described in detail. The auto-correlation function of scattering electric field is measured in the light scattering method. The auto-correlation D function of scattering electric field is indicated by following Eq. 1:

$$g^{(1)}(\tau) \quad \text{(Eq. 1)}$$

"$\tau$" is correlation time. Assuming $t_1$ and $t_2$ as the times two photon pulses are respectively detected in detector 330, the correlation time $\tau$ of the two photon pulses is an absolute value of a difference between $t_1$ and $t_2$ ($|t_1-t_2|$). When light scattering is carried out in a turbid solution obtained by dispersing fine particles with uniform particle diameters in high concentration, multiple scattering occurs where the incident light is scattered a plurality of times in the solution. It is known that the theoretical equation is indicated by Eq. 2 in such multiple scattering, for example, as described in the following document: D. A. Weitz and D. J. Pine, "Diffusing-Wave Spectroscopy in Dynamic Light Scattering", ed. W. Brown, ch. 16, Oxford Science Pub., 1993, p. 652-720:

$$g^{(1)}(\tau) \cong \exp(-2k_0^2 N(l) D\tau)(N \geq 2) \quad \text{(Eq. 2)}$$

where $k_0$ is a magnitude of a wave number vector of incident light, $N(l)$ is the number of scattering times in multiple scattering, l is an optical path length, and D is a diffusion coefficient of a fine particle.

Since a shorter optical path length decreases the number of scattering times, Eq. 3 is obtained in principle.

$$\lim_{l \to 0} N(l) = 1 \quad \text{(Eq. 3)}$$

Meanwhile, in light scattering in a transparent solution obtained by dispersing fine particles with uniform particle diameters in low concentration, the incident light is scatted only once. It is known that the theoretical equation is indicted by Eq. 4 in such single scattering.

$$g^{(1)}(\tau) \cong \exp(-q^2 D\tau)(N=1) \quad \text{(Eq. 4)}$$

where q is a magnitude of a scattering vector.

It is noted in the present invention that Eq. 2 of multiple scattering and Eq. 4 of single scattering become the same expression when the scattering angle $\theta$ is fixed to 90° ($\theta=90°$), because the scattering vector q agrees with the wave number vector $k_0$, and N becomes 1 (N→1) under the condition of the optical path length l being 0 (l→0). In other words, Eq. 6 is obtained when $\theta$ is 90° (θ=900) from Eq. 5, and Eq. 2 and Eq. 4 become the same equation as indicated by Eq. 7.

$$q = 2k_0 \sin\frac{\theta}{2} \quad \text{(Eq. 5)}$$

$$q^2 = 2k_0^2 \quad \text{(Eq. 6)}$$

$$g^{(1)}(\tau) \cong \exp(-2k_0^2 N(l) D\tau)(N \geq 1) \quad \text{(Eq. 7)}$$

Accordingly, by performing measurement while fixing the scattering angle $\theta$ to 90° ($\theta=90°$), Eq. 7 can be used in the case of arbitrary optical path length l.

In such theoretical background, by measuring the auto-correlation function (Eq. 1) of scattering electric field while varying the optical path length l, obtained is the auto-correlation function in agreement with single scattering under the extreme condition of the optical path length l being zero (l→0). By this means, the same analysis method as in single scattering can be applied to turbid samples such that multiple scattering occurs.

Figure 4:
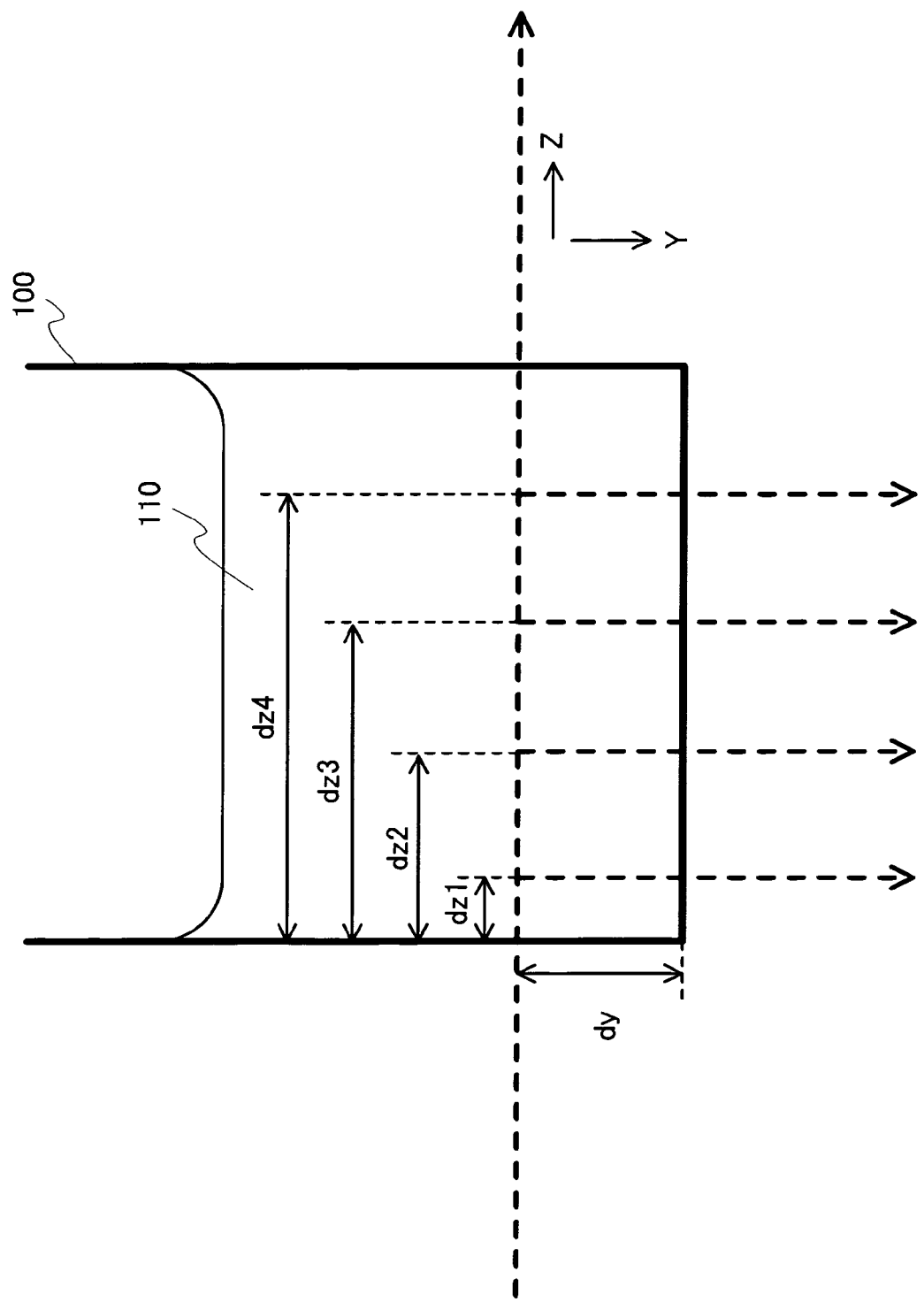
FIG. 4 is a view showing an example of positions to measure.
Figure 5:
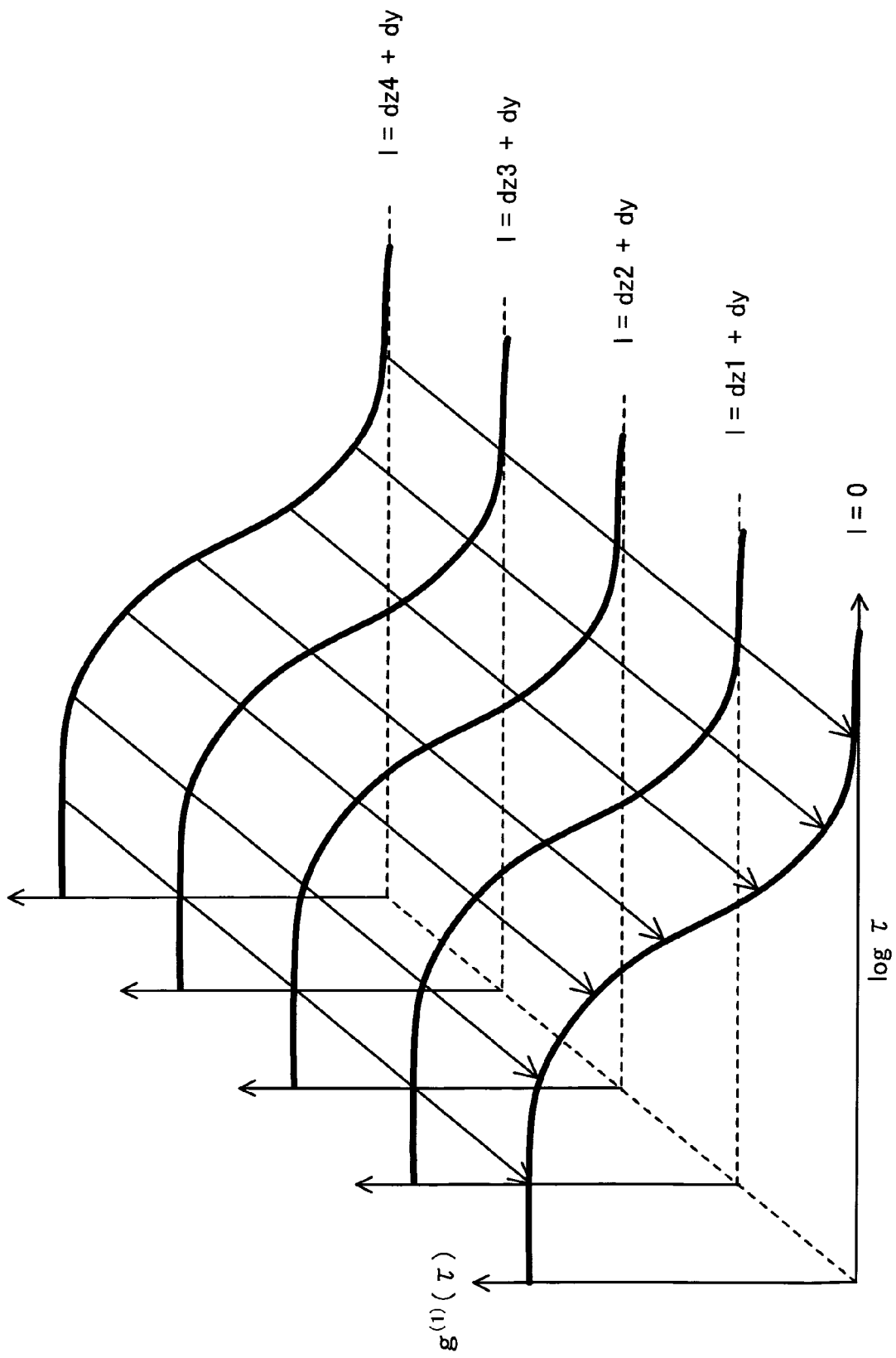
FIG. 5 is a view showing in time series the relationship between logarithm of correlation time and a photon correlation function of scattering electric field.
Figure 6:
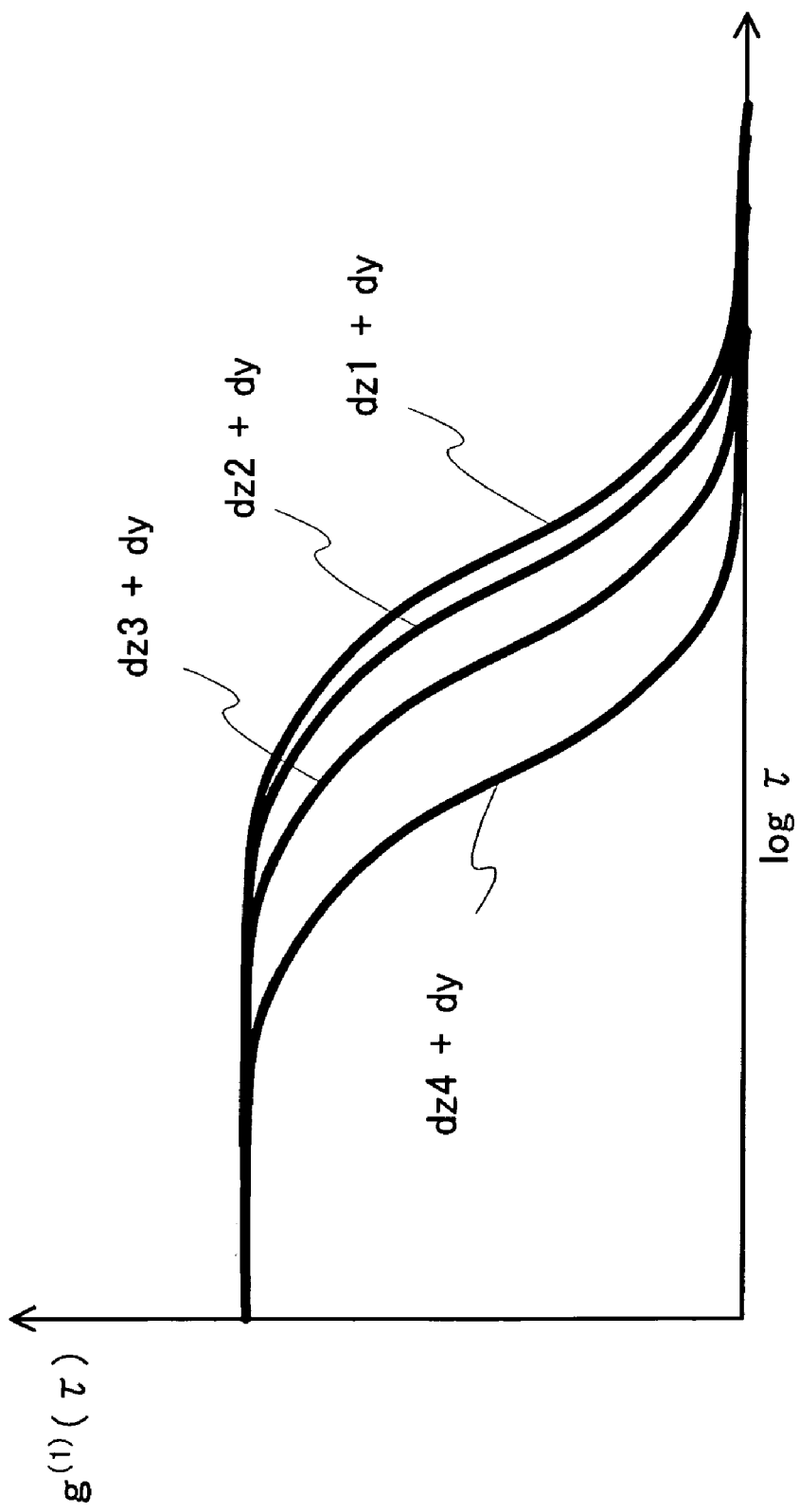
FIG. 6 is a view resulting from projection of FIG. 5 to a plane of optical path length l of zero (l=0)

The measurement principles as described above are explained with reference to FIGS. 4 to 6. FIG. 4 is a view showing an example of positions to measure. FIG. 5 is a view showing in time series the relationship between logarithm of correlation time and an auto-correlation function of scattering electrical field. FIG. 6 is a view resulting from projection of FIG. 5 to a plane of optical path length l of zero (l=0).

As shown in FIG. 4, the incident laser light is incident in the Z-axis direction, while the scattered light is scattered in the Y-axis direction. The optical path length l is dz+dy, dy is assumed to be a currently maximum value, 1 mm. The incident laser light dz in the Z-axis direction is measured with respect to four kinds such that the relationship in length is dz1<dz2<dz3<dz4, while control section 190 scans the position of sample cell 100.

FIG. 5 is a graph showing measurement results on four kinds as shown in FIG. 4, and calculated data with extrapolation of the optical path length l to zero (l=0) based on the measurement results. FIG. 5 shows four kinds of data with values of the optical path length l. Similarly, FIG. 6 also shows four kinds of data with values of the four kinds of data indicated ("l" is omitted in description). As shown in FIGS. 5 and 6, as the optical path length l is gradually decreased, the number of scattering times N approaches "1". Therefore, it is possible to calculate by extrapolation the auto-correlation function (Eq. 1) of the case where the optical path length l is zero (l=0: dz=0 and dy=0), in other words, of the case of single scattering.

By thus extrapolating results measured on a plurality of different optical path lengths l from zero to a predetermined range, the auto-correlation function of single scattering is calculated. The predetermined range is less than a cell length a, preferably less than or equal to a/2. The number of a plurality of optical path lengths l is preferably at least three or more. The measurement principles are as described above.

Calculation of photon correlation function (auto-correlation function of scattered light intensity) will be described below.

As a method of calculating the auto-correlation function (Eq. 1) of scattering electric field from time-series data of photon pulses, there is a method of obtaining a histogram of time spacings of photon pulses. Assuming detection times of an ith photon pulse and jth photon pulse as $t_i$ and $t_j$, respectively, the time spacing between the two photons is indicated by $S=|t_i-t_j|$ (absolute value of $t_i-t_j$). The frequency is counted on all the time spacings S, and the distribution function (or histogram) P(S) is obtained. P(S) is the photon correlation function, equivalent to the auto-correlation function of scattering light intensity indicated by Eq. 8, and proportional thereto when S=τ.

In other words, the relationship of Eq. 9 is obtained. Siegert equation is used in obtaining Eq. 1 from Eq. 8 (see Non-patent Documents 1 and 2). Then, the relationship is obtained such that the histogram P of photon spacing (S; $\tau_{i-1} < S \leq \tau_i$)=photon correlation function $g^{(2)}(\tau_i)$=photon correlation function $g^{(2)}(\tau_i)$ of scattered light intensity (as discrete measurement data).

$$g^{(2)}(\tau) \quad \text{(Eq. 8)}$$

$$g^{(2)}(\tau) = \frac{P(\tau)}{P_0} \quad \text{(Eq. 9)}$$

where $\tau$ is the correlation time, and $P_0$ is a constant.

$P_0$ is determined using characteristics of $g^{(2)}(\tau)$ so that $g^{(2)}(0) = 2$.

In addition, in the following descriptions, the correlation function is determined as follows: $g^{(1)}(\tau)$ indicated in (Eq. 1) is the auto-correlation function of scattering electric field, and the auto-correlation function, i.e. photon correlation function of scattered light intensity $g^{(2)}(\tau)$ indicated in (Eq. 8). In addition, describing merely as "correlation function" means n-order correlation function $g^{(n)}(\tau)$ (integers of $n \geq 1$), and is of concept including both $g^{(1)}(\tau)$ and $g^{(2)}(\tau)$.

Conventionally, in the case of obtaining Eq. 9 by a calculation method, detection times of photon pulses are input to a computer as time-series data, and the photon correlation function P(S) is calculated. By improving the method, a new method has been proposed of calculating the photon correlation function P(S) at high speed.

Figure 7:
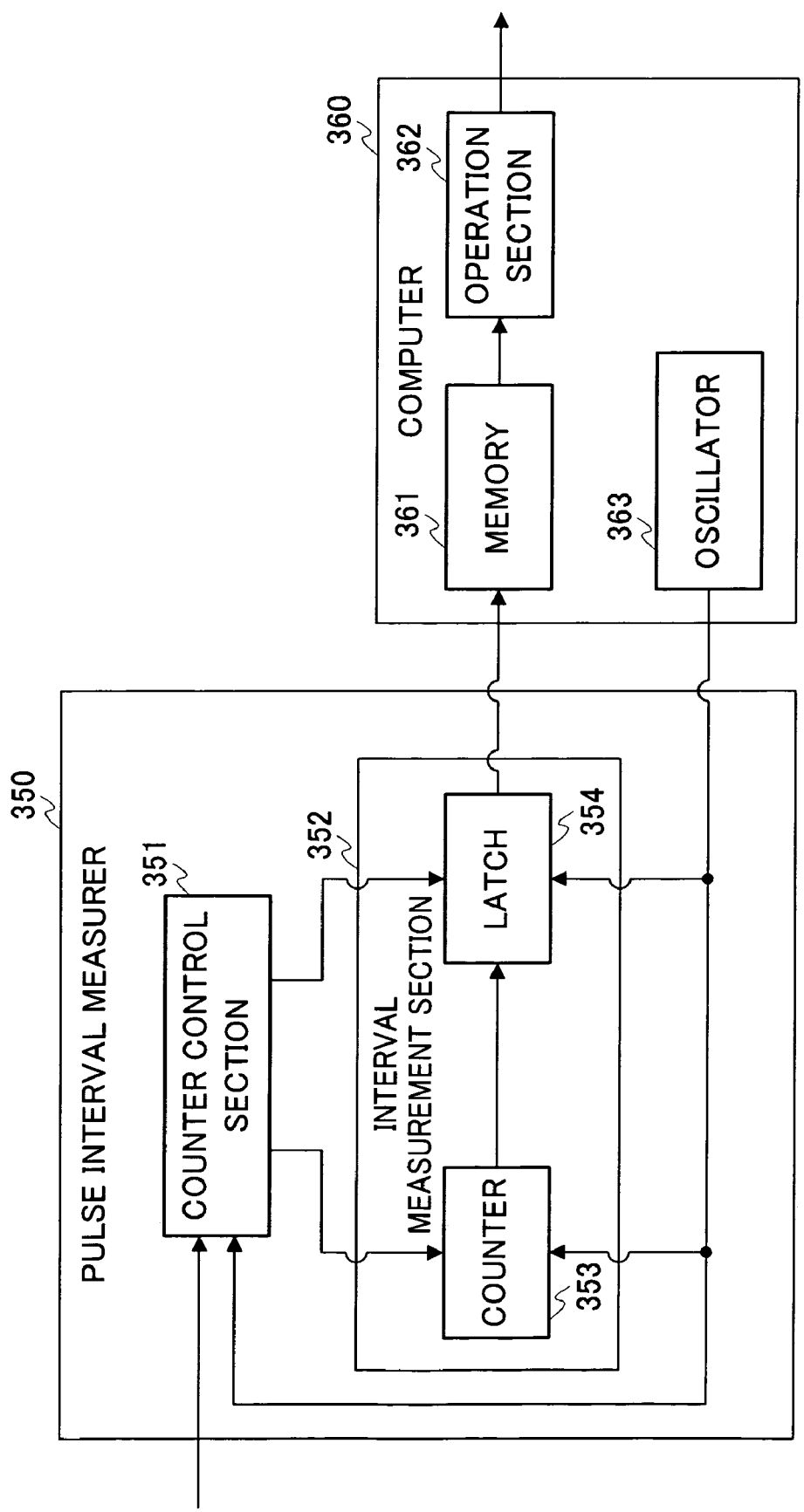
FIG. 7 is a view showing an example of configurations of a pulse interval measurer and a computer.
Figure 8:
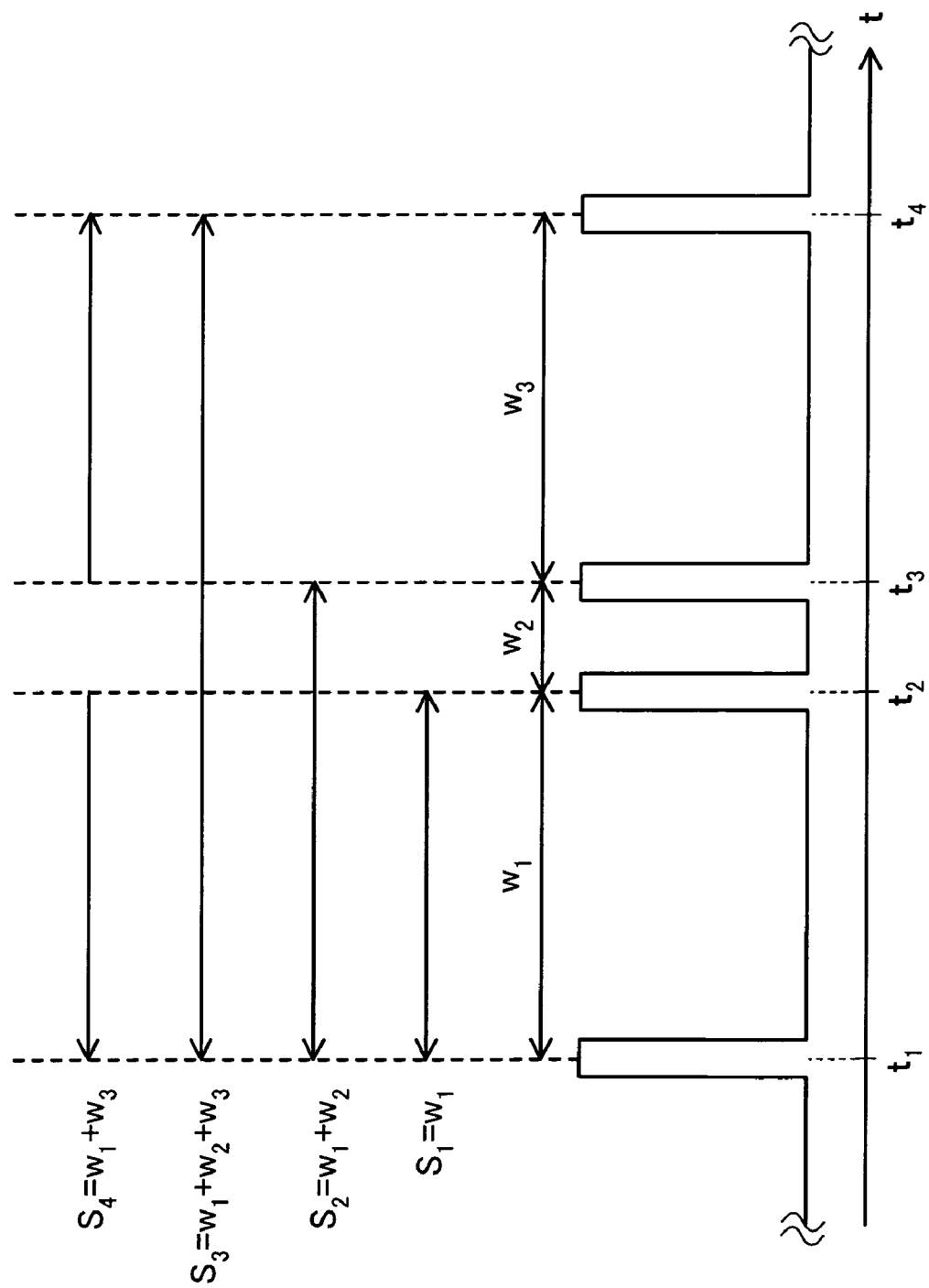
FIG. 8 is a view to explain time spacings.

The method of calculating the photon correlation function at high speed will be described below with reference FIGS. 7 and 8. FIG. 7 is a view showing an example of configurations of pulse interval measurer 350 and computer 360. FIG. 7 shows structural elements on the function of calculating the photon correlation function, and omits on the other functions. The elements with the same reference numerals as in FIG. 3 have the same functions as in FIG. 3, where pulse interval measurer 350 measures a time interval of photon pulses, and computer 360 is used to calculate a value of the photon correlation function from measured time intervals. FIG. 8 is a view to explain time interval and spacing.

Pulse interval measurer 350 includes counter control section 351, and interval measurement section 352.

Counter control section 351 controls timing to measure a photon pulse interval. Specifically, when a photon pulse is input, counter control section 351 instructs time interval measurement to interval measurement section 352.

Interval measurement section 352 measures a time interval of two adjacent photon pulses (time interval between input of one photon pulse and input of next photon pulse) to notify computer 360. The section 352 is provided with counter 353 and latch 354 as an output circuit Computer 360 includes memory 361, operation section 362 and oscillator 363. Not shown in FIG. 7, but computer 360 has a Central Processing Unit (CPU) and storage area. The CPU controls the entire processing (including processing and execution of operation section 362) of computer 360, and the storage area is to store, read and/or write data when each processing is executed.

Memory 361 is First-In First-Out (FIFO) buffer memory. A commercially available digital input/output board is used as an input circuit.

Operation section 362 calculates the photon correlation function using time intervals of photon pulses stored in memory 361.

Oscillator 363 makes standard time and generates a system clock signal. A quartz oscillator is used as an example thereof.

The operation will be described below.

Counter control section 351 inputs a photon pulse into a digital circuit, and interval measurement section 352 measures a time interval $w_i = |t_i - t_{i+1}|(i>0)$ of adjacent two photon pulses. FIG. 8 shows specific examples of time interval $w_i$. Counter 353 measures the time interval $w_i$ by counting up at timing at which a system clock is input from oscillator 363. At the time counter control section 351 instructs interval measurement, latch 354 stores a value of counter 353 temporarily, and then, outputs the value to memory 361. The time interval $w_i$ measured by interval measurement section 352 is input to memory 361. Memory 361 stores time-series data of time interval $w_i$ of photon pulses.

Operation section 362 calculates the time spacing of two photon pulses from the time-series data of the time interval $w_i$, and calculates the histogram P(S). The time spacing S of two photon pulses is a spacing between timing of input of one photon pulse and timing of input of another photon pulse, and includes cases where inputs of two photon pulses are not adjacent. Accordingly, the spacing is also referred to as the sum of successive time intervals $w_i$. FIG. 8 shows four kinds, $S_1$ to $S_4$, where $S_1$ to $S_3$ are time spacings S, and $S_4$ is excluded from the time spacing S of two photon pulses.

Operation section 362 calculates the time spacing S of photon pulses from Eq. 10, while accumulating P(S).

$$S = \sum_i w_i \quad \text{(Eq. 10)}$$

Since the number of pulse intervals increases in proportion to S as S increase, using all the intervals to accumulate results in enormous calculation time. Meanwhile, instead of using all the data, even when data is thinned out to use as the time spacing increases, precision in calculation does not deteriorate. Therefore, the number of calculation times is decreased in inverse proportion to S. In the embodiment, the system clock is 10 MHz, and the lower limit of the time interval is 0.1 μs. However, since the upper limit of the correlation time to practically measure is about 1 sec, the number of combinations of photon pulses to calculate is 1 sec/0.1 μs ($=10^7$ times) in comparison between the lower limit and upper limit, and results in an enormous amount of calculation. In using the method of thinning out data newly proposed in the specification, the calculation time between the lower limit and upper limit is about $10^3$ times even in consideration of calculation time for thinning. Accordingly, the calculation time of histogram P(S) is accelerated by $10^4$ times.

$$g^{(2)}(0) = 2 \quad \text{(Eq. 11)}$$

Eq. 9 is used to calculate Eq. 11 from P(S), but it is simple calculation and dose not relate to loss of calculation time at all.

The calculation will be described below. Pulse interval measurer 350 counts input photon pulses, and outputs counted data to computer 360. Using the counted data of photon pulses, computer 360 calculates the photon correlation function on each data of photon pulses with different optical path lengths l, extrapolates values of n-order correlation function $g^{(n)}(\tau)$ obtained from photon correlation functions with different optical path lengths l, and calculates the n-order correlation function of the case where the optical path length 1 is zero. The specific calculation method will be described below.

Figure 9:
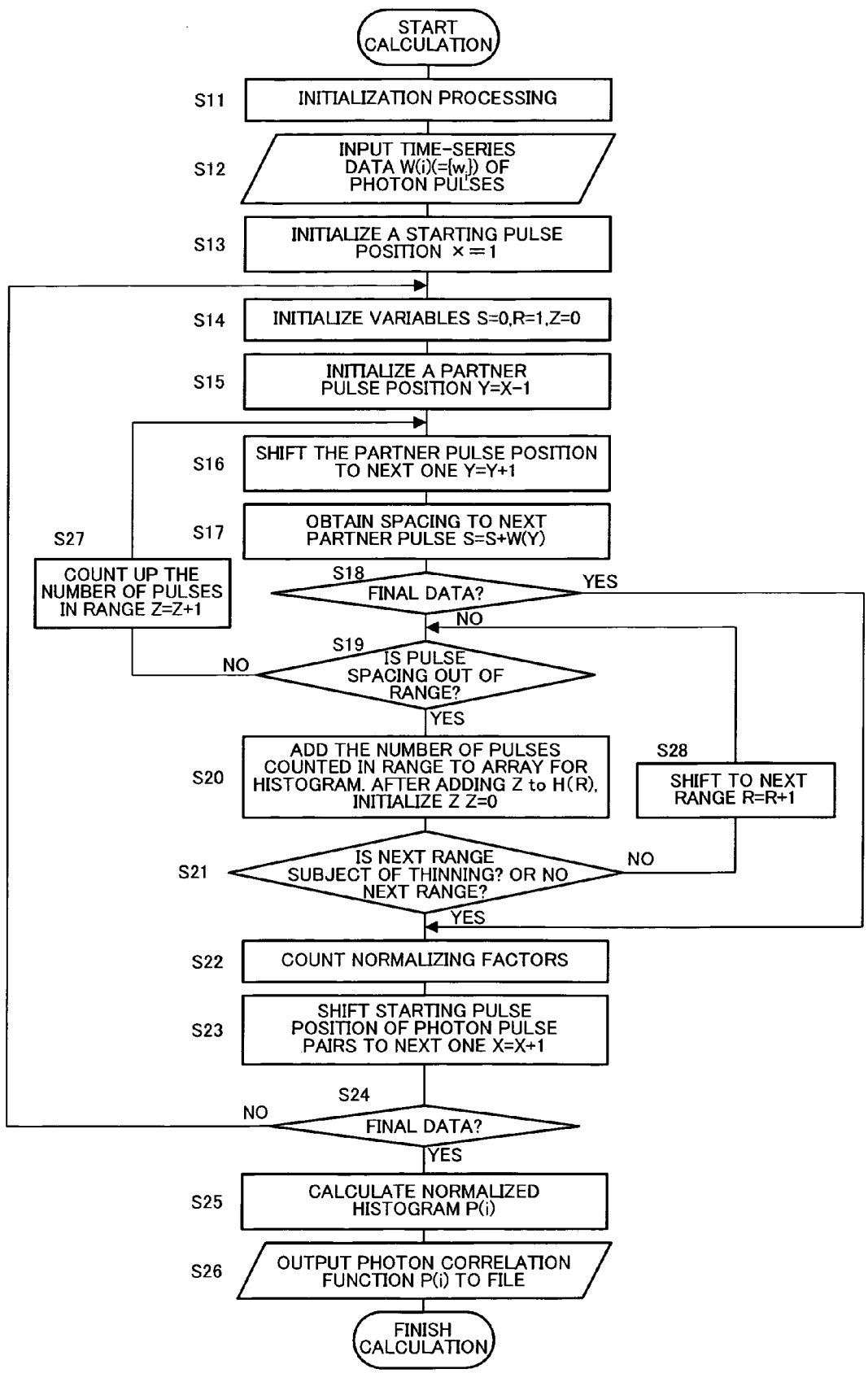
FIG. 9 is a flow diagram illustrating an example of operation to calculate a photon correlation function.

Calculation of the photon correlation function will be described first. FIG. 9 is a flow diagram illustrating an example of operation of calculating the photon correlation function. The analysis program first calculates the following histogram:

$$P(S; \tau_{i-1} < S \leq \tau_i) (i=1, 2, \ldots n)$$

Herein, $\{\tau_i\}$ is a progression to determine a range of each element of the histogram, and if, for example, a geometric progression, defined as in Eq. 12.

The range indicates a width of predetermined time.

$$\tau_i = \tau_0 \times \left(\frac{\tau_n}{\tau_0}\right)^{\frac{i}{n}} \quad (i = 1, 2, \ldots, n) \tag{Eq. 12}$$

At this point, the range of an ith range is defined by region $(\tau_{i-1}, \tau_i)$. The histogram is a distribution function representing the number of photon pulse spacings S per each range, and directly corresponds to the photon correlation function. The histogram $P(S; \tau_{i-1} < S \leq \tau_i)$ is specifically an array consisting of n numeric values, and also expressed as $P(i)$ (i=1, 2, . . . ,n).

The specific operation will be described below with reference to FIG. 9. In FIG. 9, a starting pulse is a pulse as a starting point in calculating the histogram of time spacing, and a partner pulse is a pulse subsequent to the starting pulse. In FIG. 8, assuming the starting pulse as $t_1$, $t_2$, $t_3$ and $t_4$ are partner pulses, and assuming the starting pulse as $t_2$, $t_3$ and $t_4$ are partner pulses.

Operation section 362 performs initialization processing (S11). Specifically, prior to calculation, operation section 362 prepares histogram accumulating array H(i) for use in accumulation of histogram and normalizing array M(i) (S; $\tau_{i-1} < S \leq \tau_i$) to normalize H(i). Array H(i) means array H(S; $\tau_{i-1} < S \leq \tau_i$), while array M(i) means array M(S; $\tau_{i-1} < S \leq \tau_i$). Elements of the arrays are initialized to all zero. Further, the section 362 prepares a progression T(i)(={$\tau_i$}) to determine a range of array elements. T(i) is a geometric progression. These arrays use the predetermined storage area of computer 360. Further prepared are variables for calculation loop, X, Y, S, R and Z. X represents a starting pulse position of a photon pulse pair, Y represents a partner pulse position of the photon pulse pair, S represents the sum of photon pulse intervals, R represents a variable indicating a range of an array, and Z represents a counter of the number of pulses in the range. The photon pulse pair indicates a pair of the starting pulse and the partner pulse.

Operation section 362 reads the time-series data of photon pulses stored in memory 361 in the array W(i) (S12), and then, initializes the variable X representing the starting pulse position of the photon pulse to "1". That is, the section 362 selects a first photon pulse (S13). Variables for calculation loop are initialized (S=0, R=1 and Z=0) (S14). Further initialized is the partner pulse position of a photon pulse pair of the starting pulse (Y=X+1) (S15).

The partner pulse position of the photon pulse pair is shifted to next one (S16), and the time spacing until a next pulse comes is obtained from S=S+W(Y) (S17). At this point, when a photon pulse is not input to pulse interval measurer 350, correspondence is as described below. When a photon pulse is not input to pulse interval measurer 350 for a predetermined period of time, counter 353 becomes full count (for example, (FFFF)$_{16}$ in 16 bit binary counter). In this case, regarding as a photon pulse not inputting to pulse interval measurer 350, pulse interval measurer 350 outputs data with a value of 0 to computer 360. In consideration of the data, operation section 362 in computer 360 calculates (for example, ignores the data) the time spacing S of two photon pulses, and thus, is capable of overcoming.

Next, the section 362 determines whether a position of a partner pulse is final data ($W_i$ is final one stored in the memory) by judging whether Y is larger than the total number of photon pulses (Y>the total number of photon pulses) (S18), and when the data is final one ("Yes" in S18), proceeds to S22 regarding as the processing being finished in the last range. When the data is not final one ("No" in S18), the section 362 determines whether the pulse spacing is out of the range by judging S>T(R) (S19).

When the range is not changed ("No" in S19), the section 362 counts up the number of pulses (Z=Z+1) in the range (S27), and returns to S16. When the range is changed ("Yes" in S19), the section 362 adds the number of pulses counted in the range to the array for histogram. Specifically, Z is added to H (R), and Z is initialized to zero (Z=0) (S20).

It is next determined whether a next range is a subject of thinning or whether a next range exists (S21). In the calculation of photon correlation function, in order to avoid exponential increases in calculation amount with increases in time spacing, whether to calculate is selected probabilistically in shifting to a next range of H(S; $\tau_{i-1} < S \leq \tau_i$) when the time spacing of separate photon pulses increases. Such processing is referred to as "thinning". Since the calculation amount increases in proportion to increases in time spacing, thinning is to determine whether to perform calculation of a next range of H(S; $\tau_{i-1} < S \leq \tau_i$) by probability in inverse proportion to such increases. Since thinning changes the number of samples on statistics for each range, the section 362 stores the number of calculated photon pulses for each range of H(S; $\tau_{i-1} < S \leq \tau_i$), i.e. the number of photon pulse samples in M(S; $\tau_{i-1} < S \leq \tau_i$).

When "No" in S21, the section 362 shifts to the next range (R=R+1) (S28), and executes processing from S19. When "Yes" in S21, it is regarded that the calculation is finished in the last range, and normalizing factors are counted (S22). Specifically, "1" is added to M(R-1), and no processing is executed if R-1<1. Then, a starting pulse position of the photon pulse pair is shifted to a position of a next photon pulse (X=X+1) (S23). The section 362 determines whether the position is final data by judging whether X is larger than the total number of photon pulses (X>the total number of photon pulses) (S24), and when the data is not final one ("No" in S24), repeats the processing from S14, while when the data is final one ("Yes" in S24), calculating the normalized histogram P (i) using the histogram array H(i) and normalizing factor array M (i) from Eq. 13 (S25). The section 362 outputs the photon correlation function P(i) to a file to store in the storage area (S26).

$$P(S; \tau_{i-1} < S \leq \tau_i) = \frac{H(S; \tau_{i-1} < S \leq \tau_i)}{\sum_{j=1}^{i} M(S; \tau_{j-1} < S \leq \tau_j)} \tag{Eq. 13}$$

Thus, the speed of calculation of the photon correlation function (Eq. 8) can be increased by using circuits (output circuit and input circuit) for accurately measuring the time interval $W_i$ between adjacent two photon pulses $t_i$ and $t_{i+1}$ to input to the computer, and the new calculation system.

Further, a calculation circuit in interval measurer 352 and a circuit for computer 360 to input to memory 361 are synchronism circuits operating according to the system clock signal generated by oscillator 363. Accordingly, there is no risk that an error is included due to failure of input and/or excess input of time-series data.

Further, from the viewpoint of operation section 362 of computer 360, since the time-series data of time interval $W_i$ is stored in memory 361, it is possible to collectively read data in memory 361 at the time calculation is required without concern for waiting time until the time-series data is stored, improving efficiency in calculation. Furthermore, this system can be constructed inexpensively by combining a simple calculation digital circuit, general digital input/output board and personal computer.

The processing will be described below for extrapolating correlation functions respectively of a plurality of optical path lengths 1 and calculating a correlation function of an optical path length of zero. An extrapolation method will be described first, and then, specific processing will be described with reference to a flow diagram. In addition, in following descriptions of the specification, Eq. 1 is also described as "$g^{(1)}(\tau)$". Further, equations related to $g^{(1)}$ may be described similarly.

When the measurement is carried out while varying the optical path length l, obtained correlation function $g^{(1)}(\tau)$ is given as $g^{(1)}(\tau, l)$ as the function of optical path length l. As described in FIGS. 5 and 6, the correlation function $g^{(1)}(\tau)$ of single scattering is obtained by measurement, and has the relationship with $g^{(1)}(\tau, l)$ so that $g^{(1)}(\tau)=g^{(1)}(\tau, 0)$. $g^{(1)}(\tau, 0)$ is an extrapolated value, and not a measured value. Extrapolation described herein is to calculate Eq. 14 using measured value $g^{(1)}(\tau, l)$.

$$g^{(1)}(\tau, 0) = \lim_{l \to 0} g^{(1)}(\tau, l) \qquad \text{(Eq. 14)}$$

Taylor expansion is used to calculate extrapolation value $g^{(1)}(\tau, 0)$. Subjecting $g^{(1)}(\tau, 0)$ to Taylor expansion with l=0 obtains Eq. 15.

$$g^{(1)}(\tau, l) = g^{(1)}(\tau, 0) + \frac{\partial g^{(1)}(\tau, 0)}{\partial l} l + \frac{1}{2!} \frac{\partial^2 g^{(1)}(\tau, 0)}{\partial^2 l} l^2 + \cdots \qquad \text{(Eq. 15)}$$
$$= \sum_{n=0}^{\infty} \frac{1}{n!} \frac{\partial^n g^{(1)}(\tau, 0)}{\partial^n l} l^n$$

Extrapolation value $g^{(1)}(\tau, 0)$ was analyzed using the expansion equation (Eq. 15). The least square method was used in the analysis. For example, in the case of the least square method in consideration of terms up to the (n+1)th term on the right-hand side of Eq. 15, the square sum (Eq. 17) of differences (Eq. 16) is minimized.

In addition, Taylor expansion on l=0 (origin point) may particularly be referred to as Maclaurin Expansion. Actually, extrapolation value $g^{(1)}(\tau, 0)$ is calculated by the least square method in a range of n from 2 to 4.

Figure 10:
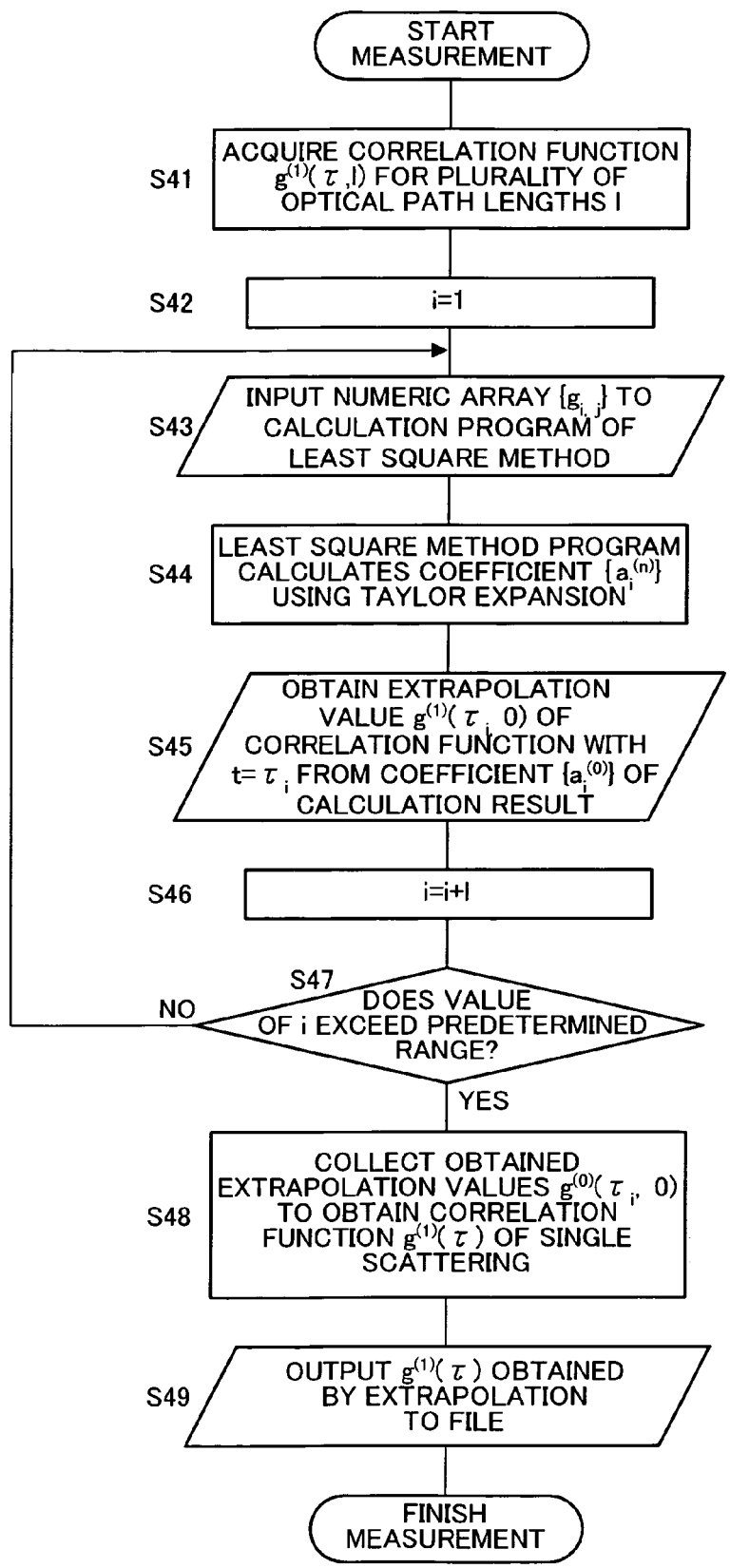
FIG. 10 is a flow diagram illustrating an example of operation of processing for extrapolating photon correlation functions with different optical path lengths.

The specific operation in the extrapolation method will be described below with reference to FIG. 10. FIG. 10 is a flow diagram illustrating an example of operation of processing for extrapolating correlation functions with different optical path lengths. The correlation functions specifically obtained by measurement are numeric values with respect to discrete relaxation time $\tau_i$ and discrete optical path length $l_j$, and represented by $g_{i,j}=g^{(1)}(\tau_i, l_j)$. "i" takes a range from 1 to the number of elements of discrete $g^{(1)}(\tau, 0)$. "j" takes a range from 1 to the number of measured optical path lengths l (the number of different optical path lengths used in measurement).

First, photon correlation functions $g^{(2)}(\tau, l)$ are obtained respectively for a plurality of optical path lengths l. These are results obtained by measuring photon pulses while varying the optical path length 1 and calculating photon correlation functions $g^{(2)}(\tau, l)$. More specifically, correlation function $g^{(1)}(\tau, l)$ is calculated using Siegert equation with respect to each of the calculated photon correlation functions $g^{(2)}(\tau, l)$, and based on the functions, the numeric array of $\{g_{i,j}\}$ is stored in memory 361 of computer 360. "{ }" means (a set of) the entire numeric array within the parenthesis. The initial value of i is set to 1 (S42).

$$\Delta_{i,j} = g_{i,j} - (a_i^{(0)} + a_i^{(1)} \cdot l_j + \cdots + a_i^{(n)} \cdot l_j^n) \qquad \text{(Eq. 16)}$$

$$S_i = \sum_j \Delta_{i,j}^2 \qquad \text{(Eq. 17)}$$

Herein, $a_i^{(n)}$ is a coefficient in polynomial expansion, and comparing with Eq. 15 results in following relationships:

$$a_i^{(n)} = \frac{1}{n!} \frac{\partial^n g^{(1)}(\tau_i, 0)}{\partial^n l} \quad (n \geq 1) \qquad \text{(Eq. 18)}$$

$$a_i^{(0)} = g^{(1)}(\tau_i, 0) \quad (n = 0) \qquad \text{(Eq. 19)}$$

The numeric array $\{g_{i,j}\}$ with measurement values is entered into a calculation program of the least square method (S43). Coefficient array $\{a_i^{(n)}\}$ is obtained which is indicated in Eq. 18 on Taylor expansion (S44). From the relationship of Eq. 19, numeric array $\{a_i^{(0)}\}$ is extrapolation value $g^{(1)}(\tau_i, 0)$ to obtain. "i" is counted up (S46), and processing of S43 to S46 is repeated until i exceeds the number of elements of $g^{(1)}(\tau_i)$ (S47)

Extrapolation values $g^{(1)}(\tau_i, 0)$ corresponding to the number of elements of $g^{(1)}(\tau_i)$ obtained in S45 are collectively given as the correlation function $g^{(1)}(\tau)$ of single scattering (S48). In other words, extrapolation values $g^{(1)}(\tau_i, 0)$ corresponding to the number of i are calculated, and using all the values results in the correlation function $g^{(1)}(\tau)$ of single scattering to obtain.

"$g^{(1)}(\tau)$" obtained by extrapolation is output to a file and stored in the storage area (S49).

When n=2, the program of the least square method calculates Eq. 20.

$$g^{(1)}(\tau_i, 0) = a_i^{(0)} = \frac{\sum_j g_{i,j} \cdot \sum_j l_j^2 - \sum_j g_{i,j} l_j \cdot \sum_j l_j}{\sum_j 1 \cdot \sum_j l_j^2 - \left(\sum_j l_j\right)^2} \qquad \text{(Eq. 20)}$$

The aforementioned explanation of the extrapolation method is described on auto-correlation function $g^{(1)}(\tau)$ of scattering electric field, but this calculation method can be applied in the same way to n-order correlation function $g^{(n)}(\tau)$ including auto-correlation function $g^{(2)}(\tau)$ of scattered light intensity, and enables calculation of the correlation function of single scattering. Specifically, n-order correlation function $g^{(n)}(\tau,1)$ is calculated from photon correlation function $g^{(2)}(\tau,1)$ in S42.

The processing of the extrapolation method in FIG. 10 is based on the general method, and is wide in applicability, but there is a more convenient extrapolation method particularly in the case where a sample is a simple system such as polystyrene-latex-particle dispersion. Described below are specific analysis procedures using two kinds of extrapolation methods, the general extrapolation method and the convenient extrapolation method. The first general extrapolation method will be described first. The first extrapolation method takes following procedures (1) to (6).

(1) Using the light scattering apparatus shown in FIG. 1 as an example, time-series data of photon pulses are measured with respect to a plurality of optical path lengths l.

(2) Using the fast calculation method of photon correlation function as shown in FIG. 9, calculated is measurement data $g^{(2)}(\tau_i)$ of the photon correlation function, i.e. auto-correlation function of scattered light intensity.

(3) On measurement data $g^{(2)}(\tau_i)$ of the photon correlation function, measurement data $g^{(1)}(\tau_i)$ of the auto-correlation function of scattering electric field is calculated using Siegert equation.

(4) The aforementioned procedures are repeated while varying the optical path length l, and determined is the optical path length l dependence of the auto-correlation function $g^{(1)}(\tau_i)$ of scattering electric field. Obtained as data is $g^{(1)}(\tau_i, l)$ (the technical idea is shown in FIGS. 5 and 6).

(5) According to explanations of S42 and subsequent steps in FIG. 10, general extrapolation calculation is performed to obtain the auto-correlation function $g^{(1)}(\tau_i) = g^{(1)}(\tau_i, 0)$ of single scattering.

(6) Various analysis methods used in the case of single scattering can be used on the obtained auto-correlation function $g^{(1)}(\tau_i)$ of single scattering.

Particularly, in the case where a sample is a simple system such as polystyrene-latex-particle dispersion, a dynamic component $\Delta g^{(1)}(\tau_i)$ of a correlation function of the obtained correlation function $g^{(1)}(\tau_i)$ is obtained using Eq. 21, and then, analyzed by fitting using the single exponential function (Eq. 22), and relaxation time $\tau_R$, is determined.

$$\Delta g^{(1)}(\tau) = \frac{g^{(1)}(\tau) - g^{(1)}(\infty)}{g^{(1)}(0) - g^{(1)}(\infty)} \quad \text{(Eq. 21)}$$

$$\Delta g^{(1)}(\tau) = \exp\left(-\frac{\tau}{\tau_R}\right) \quad \text{(Eq. 22)}$$

The second convenient extrapolation method will be described below. The second extrapolation method takes following procedures (1) to (6). The second extrapolation method is a simplified method of the first extrapolation method, and can be used in the case where the correlation function of the sample is expected to be represented by the single exponential function (Eq. 21).

(1) Using the light scattering apparatus shown in FIG. 1 as an example, time-series data of photon pulses are measured with respect to a plurality of optical path lengths l.

(2) Using the fast calculation method of photon correlation function as shown in FIG. 9, calculated is measurement data $g^{(2)}(\tau_i)$ of the photon correlation function, i.e. auto-correlation function of scattered light intensity.

(3) On measurement data $g^{(2)}(\tau_i)$ of the auto-correlation function of scattered light intensity, measurement data $g^{(1)}(\tau_i)$ of the auto-correlation function of scattering electric field is calculated using Siegert equation.

(4) A dynamic component $\Delta g^{(1)}(\tau_i)$ of measurement data $g^{(1)}(\tau_i)$ of the auto-correlation function of scattering electric field is obtained using Eq. 21, and then, analyzed by fitting using the single exponential function (Eq. 22), and relaxation time $\tau_R$, is determined.

(5) The aforementioned procedures are repeated while varying the optical path length l, and determined is the optical path length l dependence of the relaxation time $\tau_R$ (described later with reference to FIG. 15).

Figure 15:
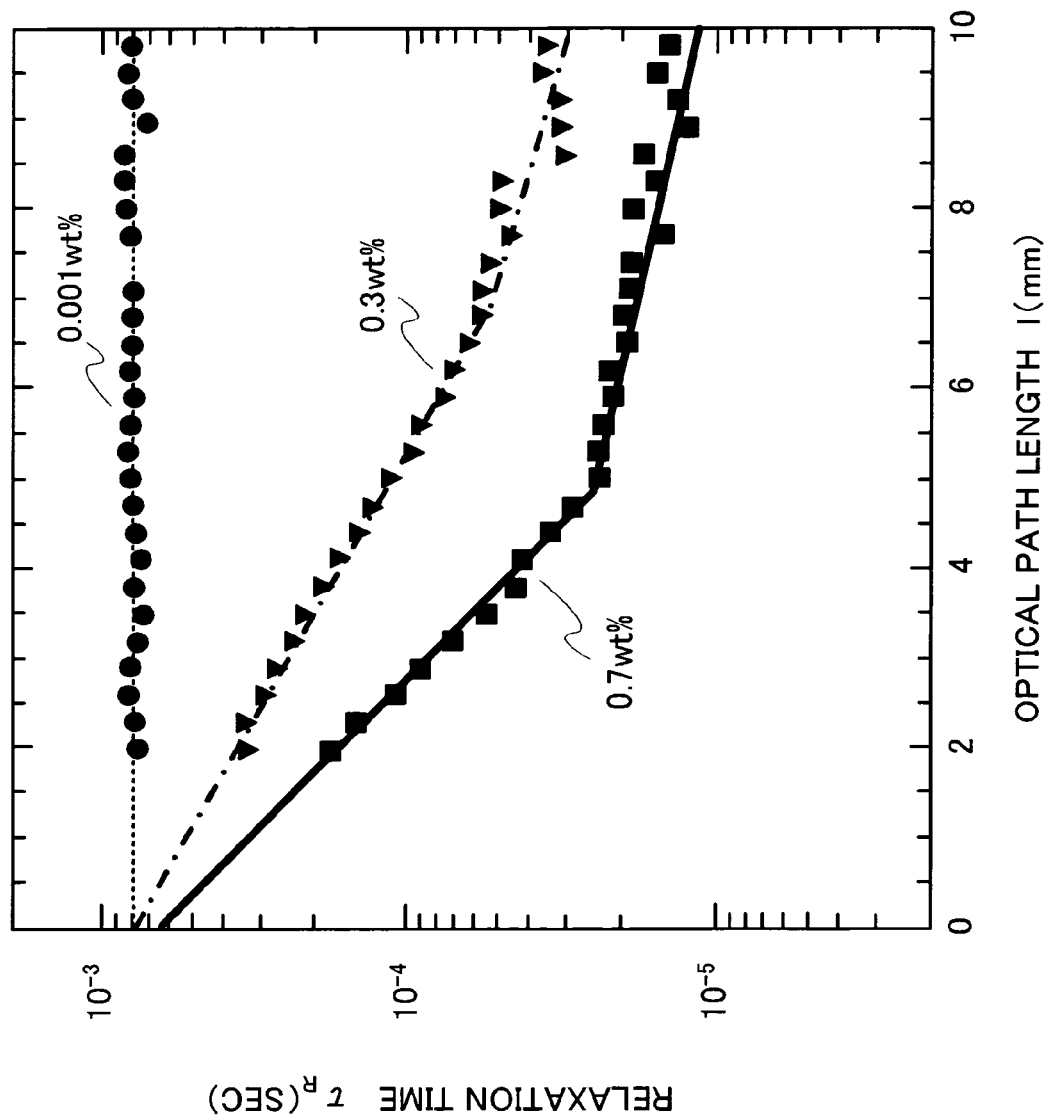
FIG. 15 is a graph showing measurement results of optical path length dependence of relaxation time.

(6) Relaxation time $\tau_R$ of single scattering on l=0 is determined by extrapolation in FIG. 15.

Particularly in the case where a sample is a simple system such as polystyrene-latex-particle dispersion, the relaxation time $\tau_R$ agrees with the relaxation time $\tau_R$ of single scattering obtained by the first extrapolation method.

The operation as shown in FIGS. 9 and 10 is specifically executed by operation section 362 according to an analysis program. The analysis program can be stored in a storage medium, and an executable program by being loaded on computer 360.

Figure 11:
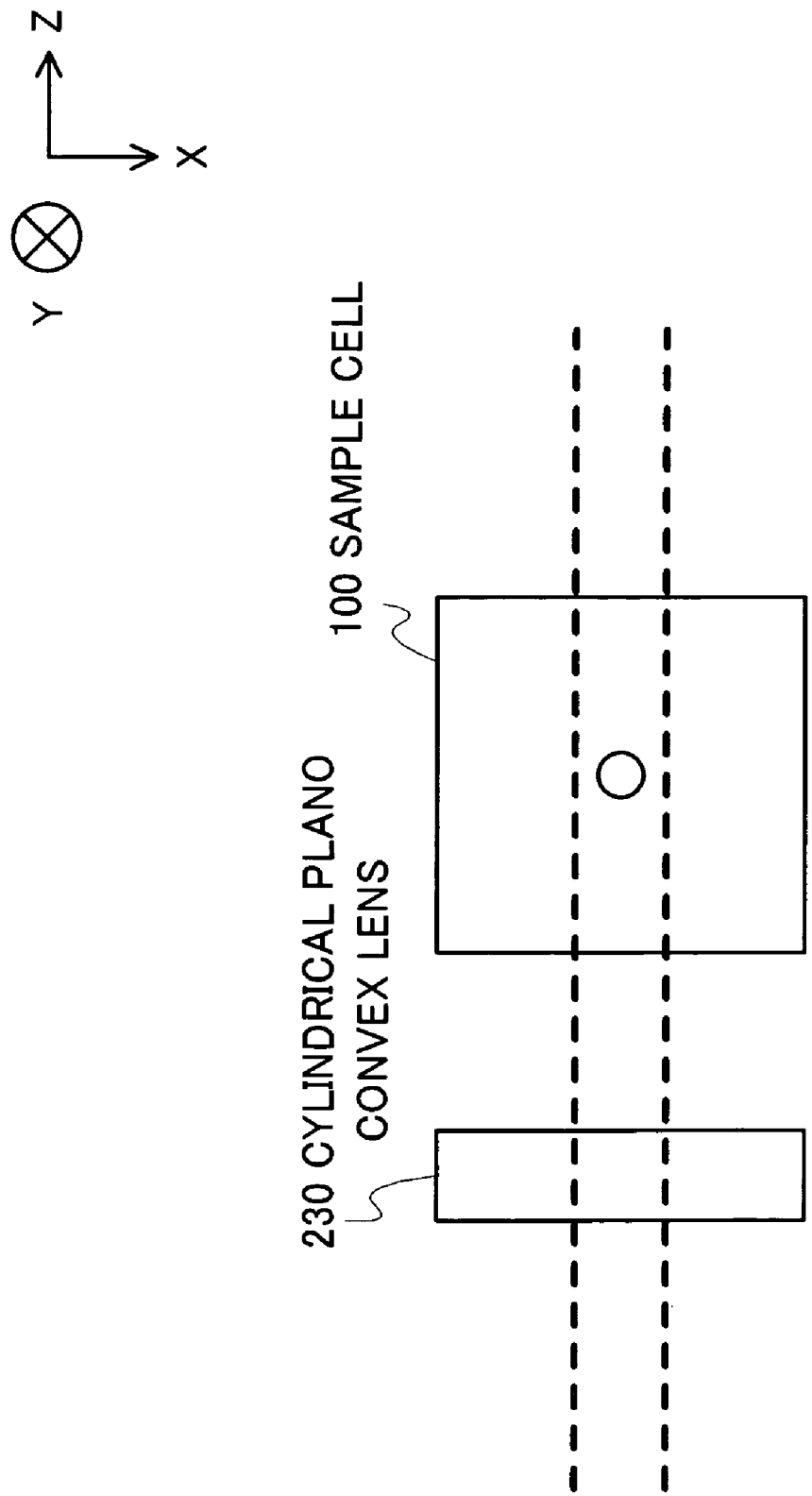
FIG. 11 is a view to explain advantages of applying a cylindrical plano convex lens (viewed from above to under in the Y-axis direction)
Figure 12:
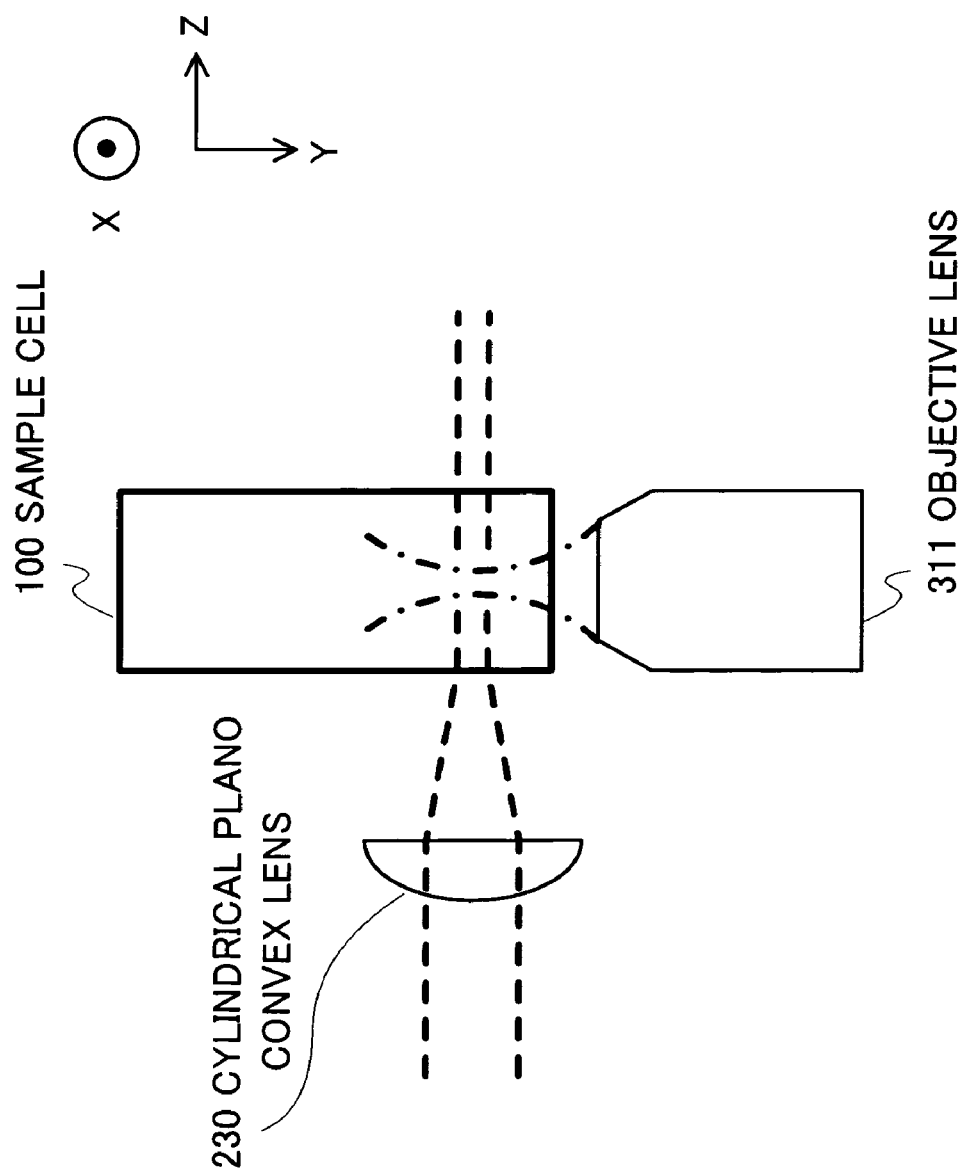
FIG. 12 is a view to explain advantages of applying a cylindrical plano convex lens (viewed from back to front in the x-axis direction)
Figure 13:
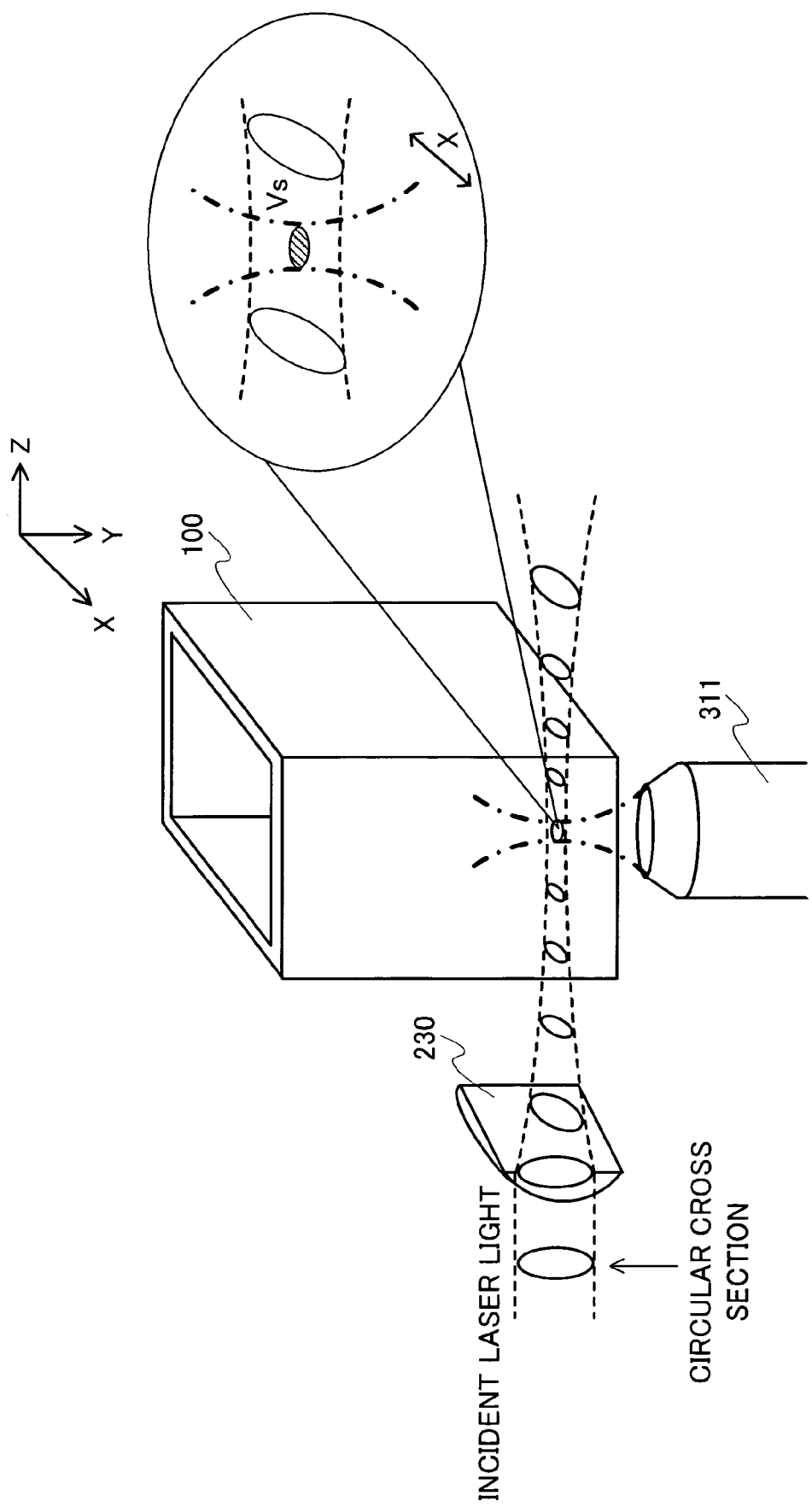
FIG. 13 is a view to explain advantages of applying a cylindrical plano convex lens (perspective view)

The effect of application of the cylindrical plano convex lens will be described below. FIGS. 11 to 13 are views to explain advantages of applying cylindrical plano convex lens 230. FIG. 11 is a view seen from above to under in the Y-axis direction, FIG. 12 is a view seen from back to front in the x-axis direction, and FIG. 13 is a perspective view. A region of the laser light seen from the Y-axis direction is not changed nor gathered (FIG. 11). Circles indicated in sample cell 100 in FIG. 11 are light-gathering points of scattered light seen from objective lens 311. The laser light seen from the X-axis direction is gathered, and confocal (FIG. 12). Thus, as shown in FIG. 11, the laser light has a circular cross section before passing through cylindrical plano convex lens 230, and has an oval cross section after passing through cylindrical plano convex lens 230. By this means, the so-called confocal structure is obtained where the focus of the laser light gathered by cylindrical plano convex lens 230 agrees with the focus of the scattered light seen from objective lens 311, and it is possible to reduce a volume of the scattering volume Vs. Further, even if objective lens 311 becomes misaligned in the X-axis direction, it is possible to enhance the possibility that the scattered light is incident on objective lens 311.

As described above, according to the light scattering apparatus and light scattering measurement method according to the present invention, it is possible to readily remove effects of multiple scattering in a sample with high turbidity, and to perform light scattering measurement with high reliability. Further, it is possible to overcome such a conventional problem that scattering of incident laser light in shallow incident depths is apt to undergo effects in vicinities of the interface between the sample and cell and is often hard to measure, and accurate data cannot be obtained. Furthermore, according to the light scattering apparatus and light scattering measurement method according to the present invention, extrapolation is carried out by varying the depth to measure, while noting the case where the scattering angle θ is fixed to 90°, it is possible to avoid effects in vicinities of the interference.

Moreover, it is possible to improve spatial resolution by reducing the control section (scanning mechanism) capable of scanning a sample in three dimensions to measure the incident depth dependence of incident light laser, and a portion to emit the laser using an objective lens. By measuring the depth dependence with respect to the theory of diffusion wave spectroscopy, it is possible to consider contributions of multiple scattering. In other words, when the scattering angle θ is fixed to 90°, it is not possible to perform measurement while varying the scattering angle, and it is not possible to perform analysis of the angle dependence in dynamic light scattering measurement.

In order to overcome this respect, using laser light with a plurality of wavelengths obtains data corresponding to conventional angle dependence from the incident wavelength dependence. Therefore, it is possible to perform analysis of the angle dependence similar to the conventional method on a structure and motion characteristics inside a sample, and to perform evaluations with high reliability. Further, emitting a plurality of kinds of laser light in time division enables more accurate measurements than emitting a plurality of kinds of laser light at the same time.

Further, substituting for conventional expensive circuitry used from the need of promptly processing enormous time-series data measured in dynamic light scattering, circuitry with performance superior to conventional one is designed using inexpensive materials, thereby reducing cost, and it is further made possible to extremely increase the speed of calculation by reducing the number of calculation processing times, thus enabling inexpensive, practical and accurate analysis.

More specifically, since the number of pulse pairs input at short time intervals is small in a region with short correlation time, it is necessary to perform calculation using all data array. Meanwhile, when the time interval exceeds 1 ms, the number of pairs of two photon pulses included in the data array remarkably increases. Accordingly, as the correlation time is longer, an excessive amount of data appears to calculate the average, and therefore, even when data is thinned corresponding to the length of time interval without using all the pairs of two photon pulses, any problem arises in precision. When the correlation time increases twice, the number of pairs of two photon pulses nearly doubles also, and therefore, half the data is used among the pairs of two photon pulses. In this way, increases in correlation time in logarithmic scale only increase an amount of calculation in proportion to the logarithm of correlation time. Thus, as longer correlation time is measured, the calculation is accelerated. This technique can be applied to other apparatus and methods, as well as the light scattering apparatus and light scattering measurement method.

In particular, it is possible to provide techniques for measuring dynamic light scattering of an opaque sample with convenience and low cost, and obtaining measurement results with high reliability on the internal structure in consideration of contributions of multiple scattering, a measurement method mainly using a microscopic scanning mechanism and multi-color laser light, a data processing method using a new electronic circuit and calculation algorithm, and an analysis calculation program to calculate a photon correlation function based on the new algorithm.

In addition, the light scattering apparatus as shown in FIG. 3 is an example, and a light scattering apparatus according to the present invention is capable of being implemented without having all the structural elements as shown in FIG. 3. For example, the apparatus may be provided with a portion having laser light source 210, sample cell 100, cell holder 180, control section 190 and a portion to controlling control section 190, and with a portion having pinhole 324 to pass scattered light scatted from sample cell 100 therethrough, detector 330, pulse interval measurer 350 and a portion for calculating a photon correlation function.

The size of sample cell 100 as shown in FIG. 2 is an example, and a sample cell may not have a rectangular bottom.

Structural elements to calculate a photon correlation function can be provided as part of the light scattering apparatus as shown in FIG. 3, and may be provided as a photon correlation function calculation apparatus by separating a portion to measure scattered light. Structural elements to measure scattered light may be provided as a light scattering apparatus without a portion to calculate a photon correlation function.

As the structural elements to calculate a photon correlation function (photon correlation function calculation apparatus), needed are pulse interval measurer 350 and a portion to calculate a photon correlation function, and pulse interval measurer 350 starts operating by receiving a photon pulse.

As the structural elements to calculate a photon correlation function (photon correlation function calculation apparatus), the portion to calculate a photon correlation function is capable of implementing the function by receiving data from a storage medium storing time-series data of time intervals of two photon pulses. In this case, a computer may be used that reads data of the storage medium and has the calculation capability. As the structural elements to measure scattered light, needed are laser light source 210, sample cell 100, control section 190 and detector 330. Control section 190 is hard to control by mutual, and it is practical to require a portion corresponding to a computer that controls control section 190.

In the configuration in FIG. 3, as control means for approximating the optical path length l by zero, the case is described of controlling a position of sample cell 100 (or, position of sample 110). However, not limited to such a case, the control means is capable of approximating the optical path length l by zero by controlling relative positions between laser light source 210, sample cell 100 and objective lens 311. Accordingly, the control means may control a position of laser light source 210 or a position of objective lens 311. In this case, the control means controls cylindrical plano convex lens 230 and polarizing light 240 as well as laser light source 210.

EXAMPLES

Described below are results of specific measurement.

Experiments were carried out using the light scattering apparatus shown in FIG. 3 as an example. Components used as the structural elements as shown in FIG. 3 will be described below.

A quartz cell with five transparent faces with a size of 10 mm×10 mm×50 mm was used as sample cell 100.

Cell holder 180 was made of brass.

As control section 190, an XYZ stage was used obtained by combining three MM stages (Product number MMU-60X) of Chuo Precision Industrial Co., Ltd. The XYZ stage was allowed to perform scanning on a 1 μm basis by biaxial controller (Product number MMC-2) of Chuo Precision Industrial Co., Ltd.

As laser light source 210, used were first light source 211 that emits Helium-Neon (He—Ne) laser light ($\lambda$=632.8 nm), second light source 212 that emits semi-conductor laser light ($\lambda$=532 nm), and third light source 213 that emits Helium-Cadmium (He—Cd) laser light ($\lambda$=632.8 nm).

Used as detector 330 was a photo-multiplier tube (PMT) of Hamamatsu Photonics K.K.

Used as cylindrical plano convex lens 230 was a cylindrical plano convex lens (f=150 mm) of Sigma Koki Co., Ltd. to gather incident light for the purpose of measuring in small scattering volume.

Used as inverted light microscope 310 was an inverted metal microscope of Olympus Corporation.

As objective lens 311, in order to detect scattered light, a very-long-focus objective lens (f=8 mm) of Olympus Corporation was attached to the inverted light microscope.

Used as mirrors were a flat mirror, half mirror (reflection wavelength of 532 nm) and half mirror (reflection wavelengths of 420 nm to 540 nm) of Sigma Koki K.K.

Used as pinholes 322 and 324 were pinholes with a pinhole diameter of 400 nm of Sigma Koki K.K.

Used as polarizing plates 240 and 321 were products of Sigma Koki K.K.

A platinum resistance thermometer of Netsushin Co., Ltd. was attached for temperature measurement, an inch-size cartridge heater of Yako was attached for temperature adjustment, and thus, a thermostatic cell holder was prepared. The temperature was set and adjusted using a digital controller (Product number SR253) of Shimaden Co., Ltd. and a thyristor regulator (Product number JS-1020V) of Chino Corporation.

The light scattering apparatus was assembled on a vibration isolated table of 80 cm×60 cm and configured as shown in FIG. 3. The XYZ coordinate axes in the light scattering apparatus were set as in FIG. 3.

Incident laser light was perpendicularly incident on a side face of sample cell 100, and scattered light was detected at the angle of 90°. Cell holder 180 was attached to the XYZ stage to enable scanning in three dimensions by control of computer 360, and it was possible to measure the incident depth dependence of the scattered light. Further, by performing measurement while scanning the position, it is possible to precisely measure the correlation function of time-space average (ensemble average) (See Documents 1 and 2).

The incident light was gathered in the perpendicular direction by cylindrical plano convex lens 230, and incident on a sample. The scattered light was gathered by very-long-focus objective lens 311. Fine reduction in scattering volume is allowed by two lenses.

Three lasers with different wavelengths were adjusted in optical axis, and installed so that the light was incident on the same place of a sample. Using three lasers enable measurement of wavelength dependence of the scattered light.

Figure 14:
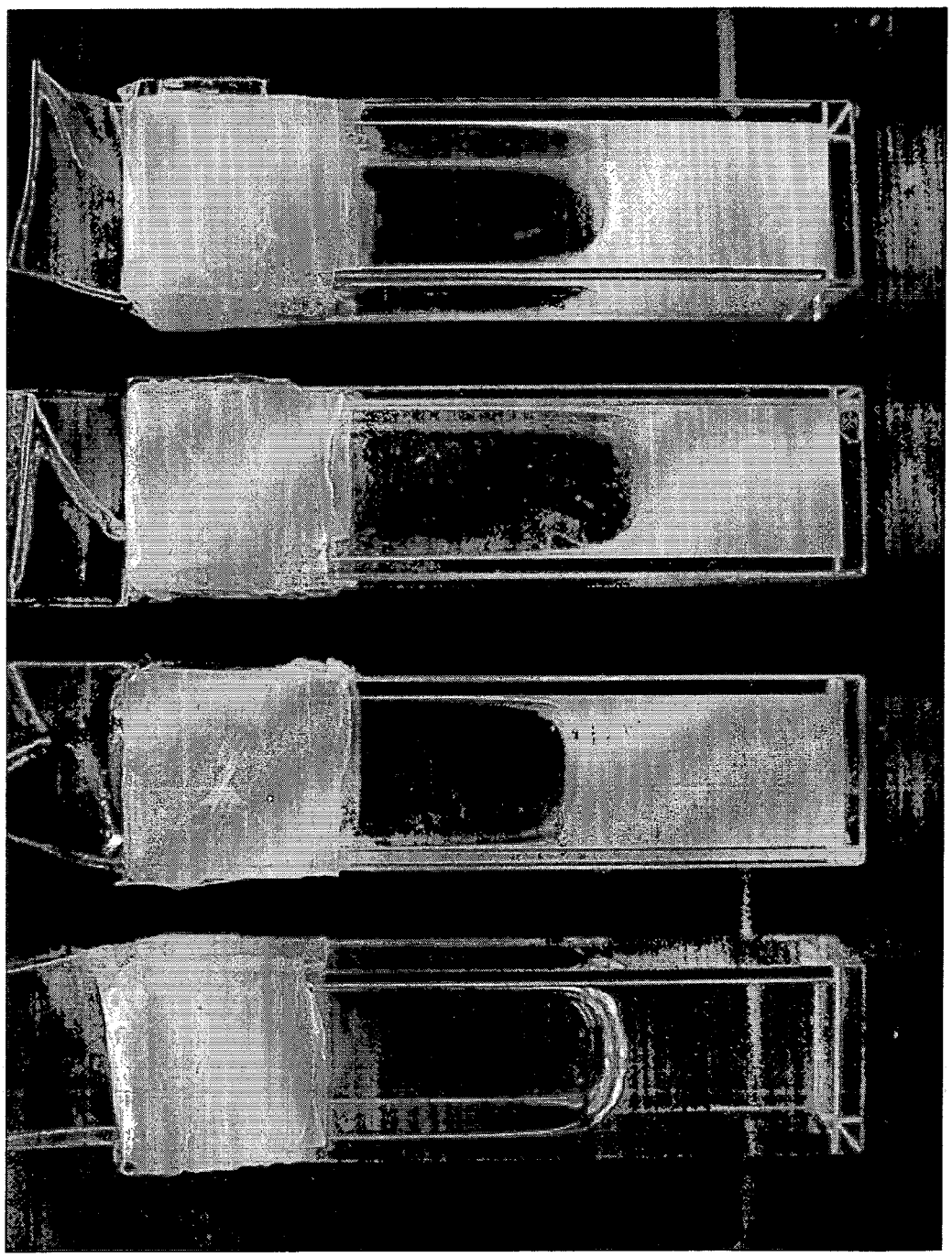
FIG. 14 is a photograph showing appearances of samples in sample cells.

Preparation of a sample (preparation of polystyrene-latex-particle dispersion) was carried out as follows: Polystyrene latex particles (particle diameter of 175 nm) were filtered with a membrane filter of 0.22 μm and then dispersed in distilled water. After mixing for a day, dispersion processing was carried out for 30 minutes by ultrasonic. Sample cell 100 for use in measurement was washed in optical measurement level to prevent the entry of fine dust, and dried adequately. The dispersion of latex particles was poured into the quarts cell while being filtered by a membrane filter of 1.2 μm, and the cell was sealed to prevent evaporation. Four concentrations, 0.001, 0.1, 0.3 and 0.7 wt % (weight percent), were prepared. FIG. 14 shows photographs of appearances of samples 100 in sample cells 110. From left to right as viewed in FIG. 14, samples with concentrations of 0.001, 0.1, 0.3 and 0.7 wt % were arranged.

Measurement results of optical path length dependence of relaxation time will be described below. In the example, the second extrapolation method was used.

With respect to the prepared polystyrene-latex-particle dispersion, measurement was carried out using the light scattering apparatus configured according to the present invention, and the photon correlation function (Eq. 8) was determined while varying the optical path length l. The dynamic component (Eq. 21) of the auto-correlation function of scattering electric field was obtained from the photon correlation function (Eq. 8). The resultant was analyzed by fitting using the single exponential function (Eq. 22).

Herein, $\tau_R$ is the relaxation time. By analysis using Eq. 22, changes in $\tau_R$ were measured with optical path length l. The measurement results were shown in FIG. 15. From the theory of multiple scattering, it has theoretically been shown that as the optical path length l increases, the number of scattering times N(l) increases, and therefore, the relaxation time $\tau_R$ decreases. Results in accordance with such phenomenon were obtained.

By extrapolating the optical path length l to the extreme condition of zero, extrapolation value $\tau_{R,0}$ of the relaxation time can be determined.

FIG. 15 shows that extrapolation values $\tau_{R,0}$ are almost the same in samples with different concentrations. It is thus indicated that the relaxation time of dispersed particles can be measured accurately even when the sample is high in concentration and turbid, and causes multiple scattering. Noting the case of 0.7 wt % with high turbidity, it is understood that as the optical path length l increases, the relaxation time $\tau_R$ rapidly decreases. Considering that measurement is carried out on the optical path length l is 2 mm (l=2 mm) using the conventional measurement method, it is understood that values of $\tau_R$ and $\tau_{R,0}$ are different nearly three times. The method exists of measuring vicinities of a surface on fine-particle dispersed liquid with high turbidity while ignoring contributions of multiple scattering (see Document 5), and is already commercially available. Based on this method, however, also from the measurement results, it is apparent that the relaxation time $\tau_R$ varies with the turbidity and optical path length, and a value may be measured which is largely different from the real relaxation time $\tau_{R,0}$.

Currently, in the case of dz=1 mm and dy=1 mm, i.e. in the case where the minimum optical path length l is 2 mm, accuracy in measurement is improved. Further, also in the case where the minimum optical path length l is 3 mm, it is known that accuracy in measurement is improved. Setting the minimum optical path length l at 2 mm is very easier than the method of measuring vicinities of a surface while ignoring contributions of multiple scattering (see Document 5), and enables cost reduction in the apparatus while facilitating (simplifying) operation in measurement.

The analysis results of wavelength dependence will be described below.

Figure 16:
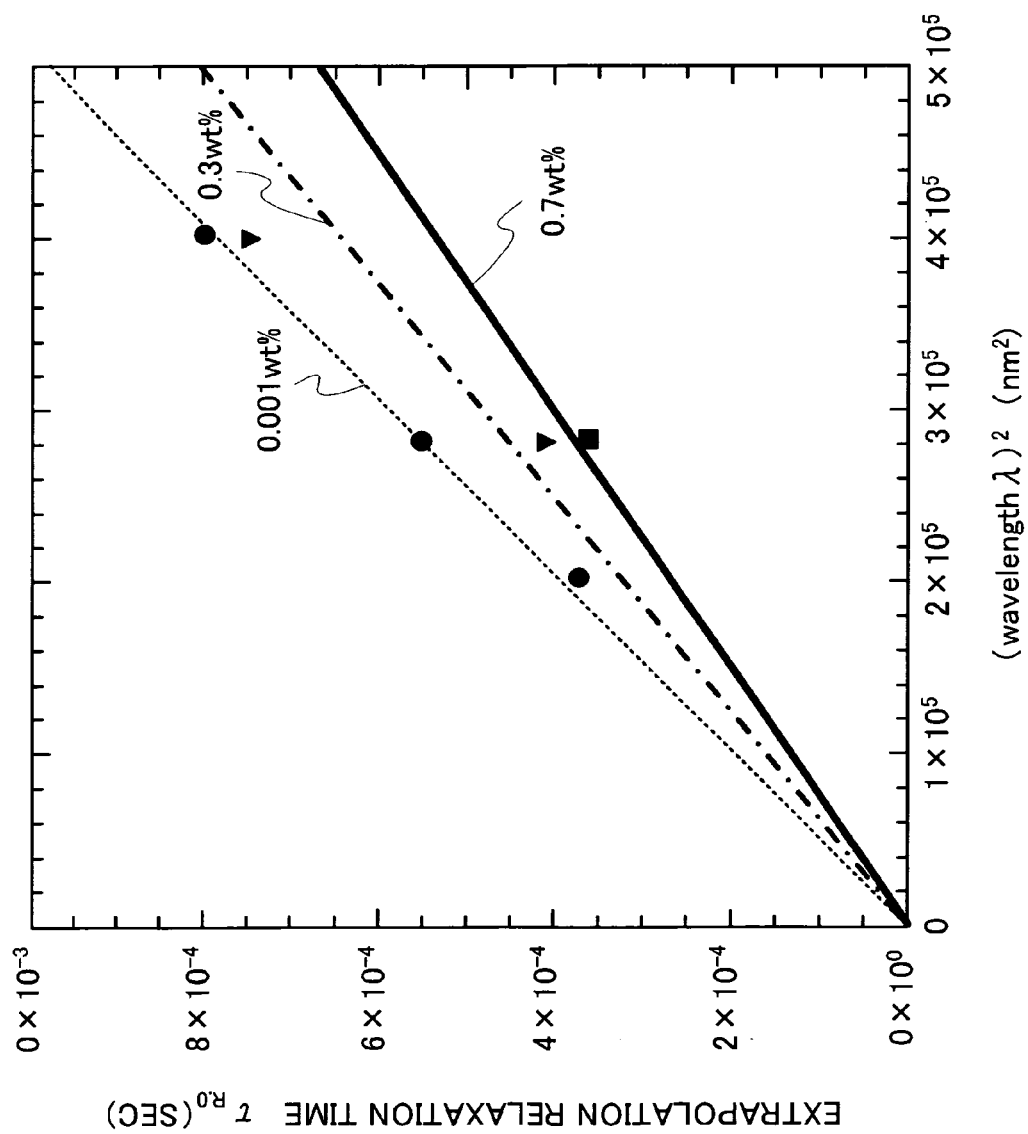
FIG. 16 is a graph showing analysis results of wavelength dependence.

Similar measurement was carried out using laser light with different wavelengths. FIG. 16 shows a plot of extrapolation value $\tau_{R,0}$ of relaxation time with square of wavelength λ of the incident light. It has been shown from the results that the wavelength dependence of the relaxation time can be measured by varying the wavelength λ of the incident light. When particles to measure are in diffusion motion, the diffusion coefficient D is estimated from the gradient of the graph. Accordingly, it is possible to determine a diffusion coefficient using a plurality of measurement values on different wavelengths of incident light, and improvements in accuracy are expected. The measurement results also show that even in the case of measuring a sample that is unknown at all, using laser light with different wavelengths enables measurement of wavelength dependence of the correlation function even when the scattering angle θ is fixed to 90°, and it is possible to examine what relaxation phenomenon occurs inside the unknown sample.

Noting the equation of multiple scattering, the number of scattering times N(l) can be measured by Eq. 23.

$$N(l) = \frac{1}{2k_0^2 D \tau_R} = \frac{\tau_{R,o}}{\tau_R} \quad \text{(Eq. 23)}$$

Figure 17:
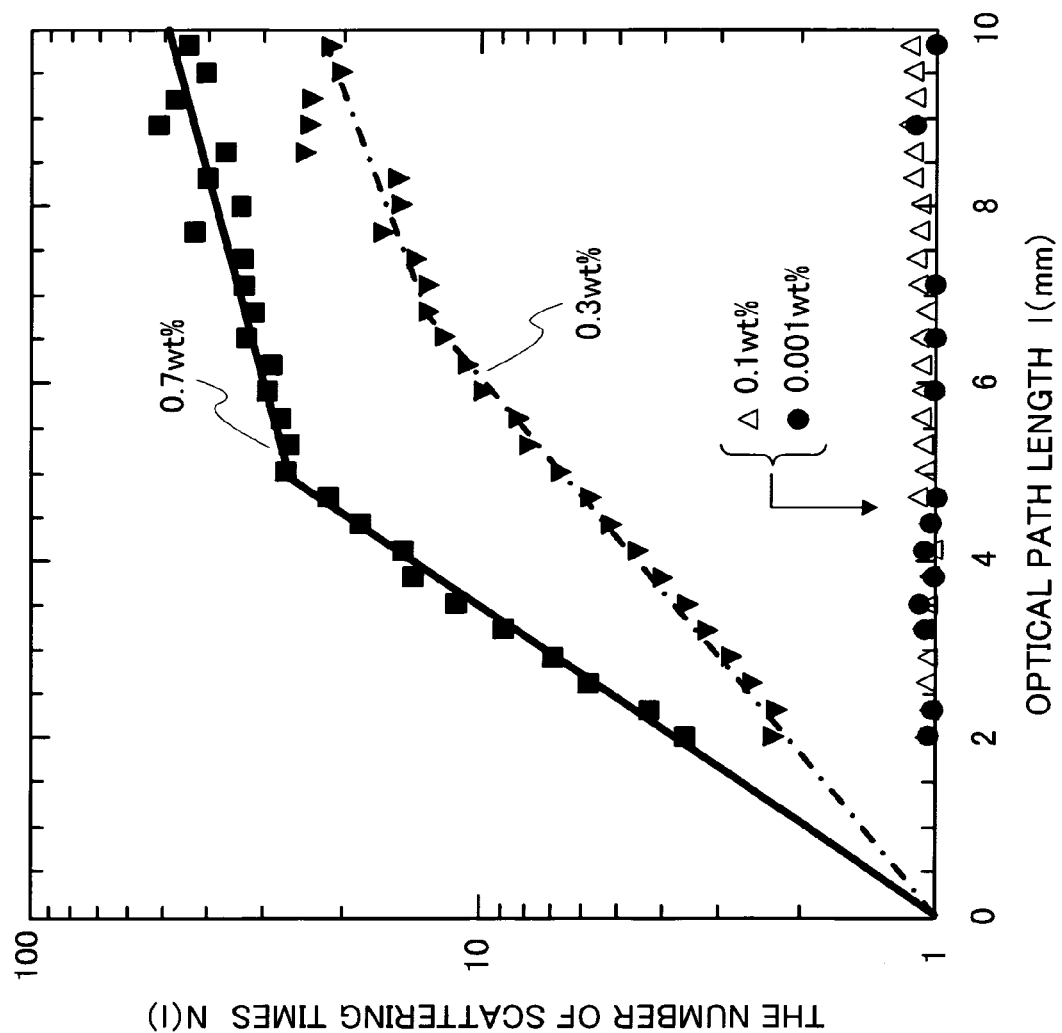
FIG. 17 is a graph showing the relationship between the optical path length and the number of scattering times.

Experimental results are shown in FIG. 17. It has been shown that the number of scattering times N(l) increases with the optical path length l, and that the shape of the graph is strongly dependent on the concentration. Such a measurement method of the number of scattering time N(l) has not existed, and it has become apparent that new measurements can be obtained by this method. It has theoretically been considered that the number of scattering times N(l) is strongly dependent on a particle diameter, shape and/or concentration of particles inside a sample (see Document 1), but there has been no specific measurement method. It is indicated that measuring the number of scattering times N(l) by this method enables acute measurement of changes in diameter and/or shape of dispersed particles without diluting a turbid sample (such as a beverage and paint), and can be applied immediately to quality control in a line of a factory and the like.

As described above, according to the present invention, D it is possible to provide the light scattering apparatus and light scattering measurement method enabling measurement of light scattering of an opaque sample. Further, it is possible to provide the inexpensive and practical method for calculating a photon correlation function from time-series data of photon pulses measured in light scattering.

The light scattering apparatus and light scattering measurement method according to the present invention have effects of enabling measurement of light scattering even when a sample is opaque, and are useful in the case of measuring an internal structure and the motion characteristics in a solid, liquid crystal, gel, colloid, polymer solution, polymer melting liquid, electrolytic solution and solution in which fine particles are dissolved such as microorganism, organelles and intracellular traits. In particular, the apparatus and method enable measurement of turbid solutions, and are capable of being applied to various fields, as a new characterization method for use in evaluations of a state of a substance in a turbid colloidal solution, a network structure inside a polymer gel, substance diffusion inside a network of a polymer gel, and the like.

The present invention is not limited to the above described embodiments, and various variations and modifications may be possible without departing from the scope of the present invention.

This application is based on Japanese Patent Application No. 2004-256056 filed on Sep. 2, 2004, entire content of which is expressly incorporated by reference herein.

What is claimed is:

1. A light scattering apparatus comprising:
a laser light source that emits laser light;
a controller that controls an optical path length required for the laser light incident on a sample to being outgoing as scattered light to approximate by zero; and
a detector that detects outgoing scattered light to output a photon pulse detection signal.

2. The light scattering apparatus according to claim 1, wherein the controller approximates the optical path length by zero by controlling a position of the sample.

3. The light scattering apparatus according to claim 1, further comprising a passing section that passes scattered light that is scattered perpendicularly to the laser light incident.

4. The light scattering apparatus according to claim 1, further comprising:
a pulse interval measurer that measures a time interval of the photon pulse output from the detector; and
an operator that calculates a photon correlation function using the time interval of the photon pulse measured in the pulse interval measurer.

5. The light scattering apparatus according to claim 4, wherein the controller varies the optical path length in stages from a predetermined value to zero, the detector detects a photon pulse corresponding to each of a plurality of optical path lengths, the pulse interval measurer measures the time interval of the photon pulse corresponding to each of the plurality of optical path lengths, and the operator calculates a photon correlation function corresponding to each of the plurality of optical path lengths, extrapolates an n-order correlation function ($n \geq 1$) obtained from the photon correlation function calculated, and thereby calculates an n-order correlation function with an optical path length of zero.

6. The light scattering apparatus according to claim 5, further comprising a memory that stores the time interval of the photon pulse measured in the pulse interval measurer on time-series data of each of the plurality of optical path lengths, and wherein the operator calculates the photon correlation function using the time interval of the photon pulse stored in the memory.

7. The light scattering apparatus according to claim 6, wherein the operator thins the time interval of the photon pulse stored in the memory in inverse proportion to the time interval of a photon to calculate the photon correlation function.

8. The light scattering apparatus according to claim 1, wherein the laser light source emits laser light with a plurality of wavelengths.

9. The light scattering apparatus according to claim 1, wherein the laser light source emits the laser light with each of a plurality of wavelengths in time division.

10. The light scattering apparatus according to claim 1, further comprising: a cylindrical plano convex lens disposed between the laser light source and the sample.

11. A light scattering measurement analysis apparatus comprising:
an input section that inputs a time interval of photon pulses obtained by measuring scattered light that is laser light incident on a sample and then scattered on each of a plurality of optical path lengths; and
an operator which calculates a photon correlation function corresponding to each of the plurality of optical path lengths using the time interval of photon pulses, extrapolates an n-order correlation function ($n \geq 1$) obtained from the photon correlation function calculated, and thereby calculates an n-order correlation function with an optical path length of zero.

12. A light scattering measurement method comprising:
a controlling step of controlling an optical path length required for laser light incident on a sample to being outgoing as scattered light to approximate by zero; and
a detection step of detecting outgoing scattered light to output a photon pulse detection signal.

13. The light scattering measurement method according to claim 12, wherein in the detection step, scattered light is detected which is scattered perpendicularly to the laser light incident on the sample.

14. The light scattering measurement method according to claim 12, further comprising:

using the photon pulse detection signal to calculate a photon correlation function.

15. A light scattering measurement method comprising:
a controlling step of controlling an optical path length required for laser light incident on a sample to being outgoing as scattered light to a plurality of optical path lengths from zero to a predetermined range; and
a detection step of detecting outgoing scattered light on each of the plurality of optical path lengths to output a photon pulse detection signal.

16. The light scattering measurement method according to claim 15, wherein in the detection step, scattered light is detected which is scattered perpendicularly to the laser light incident on the sample.

17. The light scattering measurement method according to claim 15, further comprising:
using the photon pulse detection signal to calculate a photon correlation function.

18. A light scattering measurement analysis method comprising:
an input step of inputting a time interval of photon pulses obtained by measuring scattered light that is laser light incident on a sample and then scattered on each of a plurality of optical path lengths using the time interval of photon pulses; and
an operation step of calculating a photon correlation function corresponding to each of the plurality of optical path lengths using the time interval of photon pulses, extrapolating an n-order correlation function ($n \geq 1$) obtained from the photon correlation function calculate, and thereby calculating an n-order correlation function with an optical path length of zero as a photon correlation function of scattered light intensity.

* * * * *